(12) United States Patent
Ferrari et al.

(10) Patent No.: US 9,138,512 B2
(45) Date of Patent: Sep. 22, 2015

(54) IMPLANT WITH A SURFACE LAYER HAVING A TOPOGRAPHIC MODIFICATION

(75) Inventors: Aldo Ferrari, Zurich (CH); Vartan Kurtcuoglu, Winterthur (CH); Philipp Schoen, Zurich (CH); Jens Ulmer, Zurich (CH); Alexander Borck, Aurachtal (DE); Matthias Gratz, Erlangen (DE); Alexander Rzany, Nuremberg (DE); Robert Schmiedl, Hirschaid (DE); Dimos Poulikakos, Zollikon (CH); Bjoern Klocke, Zurich (CH)

(73) Assignee: Biotronik AG, Buelach (CH)

( * ) Notice: Subject to any disclaimer, the term of this patent is extended or adjusted under 35 U.S.C. 154(b) by 3 days.

(21) Appl. No.: 13/218,120

(22) Filed: Aug. 25, 2011

(65) Prior Publication Data

US 2012/0053677 A1    Mar. 1, 2012

Related U.S. Application Data

(60) Provisional application No. 61/377,464, filed on Aug. 27, 2010.

(30) Foreign Application Priority Data

Aug. 27, 2010 (DE) .......................... 10 2010 037 194

(51) Int. Cl.
    *A61F 2/06*    (2013.01)
    *A61L 31/14*   (2006.01)
    *A61L 31/02*   (2006.01)
    *A61L 31/10*   (2006.01)

(52) U.S. Cl.
    CPC ............... *A61L 31/14* (2013.01); *A61L 31/022* (2013.01); *A61L 31/10* (2013.01); *A61L 2400/18* (2013.01)

(58) Field of Classification Search
    CPC ....... A61L 31/10; A61L 31/16; A61L 31/022; A61F 2/82
    USPC ................................................ 623/1.42, 1.46
    See application file for complete search history.

(56) References Cited

U.S. PATENT DOCUMENTS

2006/0200226 A1*  9/2006  Furst et al. ................... 623/1.15
2008/0071350 A1*  3/2008  Stinson ........................ 623/1.15
2009/0118813 A1   5/2009  Scheuermann et al.
2009/0304772 A1   12/2009 Choubey et al.
2011/0274737 A1*  11/2011 Palmaz ........................ 424/423

FOREIGN PATENT DOCUMENTS

EP     0359575 A2     3/1990
WO     2005086733 A2  9/2005

OTHER PUBLICATIONS

EP11178588.7 European Extended Search Report mailed Aug. 29, 2014.

* cited by examiner

*Primary Examiner* — Thomas J Sweet
*Assistant Examiner* — Tiffany Shipmon
(74) *Attorney, Agent, or Firm* — Wagenknecht IP Law Group PC

(57) ABSTRACT

The present invention refers to an implant with a surface layer having a topographic modification. The topographic modification includes a line pattern with ridge and groove widths of 0.9 to 1.1 μm and a ridge height of more than 0.9 μm.

13 Claims, 23 Drawing Sheets

IMPLANT WITH A SURFACE LAYER HAVING A TOPOGRAPHIC MODIFICATION

CROSS REFERENCE TO RELATED APPLICATIONS

This invention claims benefit of priority to U.S. patent application Ser. No. 61/377,464 filed Aug. 27, 2010 and German patent application serial no. 10 2010 037 194.7 filed Aug. 27, 2010 the contents of which are herein incorporated by reference in their entirety.

TECHNICAL FIELD

The present invention refers to an implant with a surface layer having a topographic modification.

TECHNOLOGICAL BACKGROUND AND PRIOR ART

US 2009/0248157 A1 provides a biocompatible substrate for cell adhesion, differentiation, culture and/or growth. The substrate having an arrangement of topographical features arrayed in a pattern based on a notional symmetrical lattice in which the distance between nearest neighbour notional lattice points is C and is between 10 nm and 10 μm. The topographical features are locally miss-ordered such that the centre of each topographical feature is a distance of up to one half of C from its respective notional lattice point.

Cell spreading on a substrate is a highly regulated process that requires the fast interaction between transmembrane receptors of the integrin family and specific ligands on the surface of the substrate (B. Geiger, J. P. Spatz and A. D. Bershadsky, *Nat Rev Mol Cell Biol*, 2009, 10, 21-33). Early receptor binding leads to onset of spreading and goes along with the enrichment of cytoplasmic proteins at the adhesion site. Here, talin, paxillin, vinculin, and several other proteins contribute to the generation of a nascent focal complex. The recruitment of activated Focal Adhesion Kinase (FAK) and Src-kinase, in turn, forms the basis of adhesion signalling (X. Zhang, G. Jiang, Y. Cal, S. J. Monkley, D. R. Critchley and M. P. Sheetz, *Nat Cell Biol*, 2008). Small, isotropic focal complexes can mature into larger focal adhesions in a process requiring myosin-II mediated cell contractility and a mechanical linkage with the actin cytoskeleton. On the other hand, insufficient integrin engagement or clustering delays spreading and/or induces cell detachment and eventually apoptosis, thus leading to an incomplete coverage of the target surface (E. A. Cavalcanti-Adam, T. Volberg, A. Micoulet, H. Kessler, B. Geiger and J. P. Spatz, *Biophysical journal*, 2007, 92, 2964-2974).

Endothelial cells (EC) spread poorly on flat, rigid implant surfaces such as those of commonly used stents for the treatment of the effects of coronary artery disease (S. Garg and P. W. Serruys, *J Am Coll Cardiol*, 2010, 56, S1-42; M. Hristov, A. Zernecke, E. A. Liehn and C. Weber, *Thromb Haemost*, 2007, 98, 274-277). Topographic modifications of the surface with micron and sub-micron scale structures may accelerate onset of spreading as well as subsequent topography-guided cell polarization (contact guidance), which are requirements for the re-establishment of a differentiated endothelium. Indeed, surface texturing of known biocompatible materials represents a promising strategy to modulate cellular processes which are essential for the development or regeneration of functional tissues (F. Guilak, D. M. Cohen, B. T. Estes, J. M. Gimble, W. Liedtke and C. S. Chen, *Cell Stem Cell*, 2009, 5, 17-26; F. Variola, F. Vetrone, L. Richert, P. Jedrzejowski, J. H. Yi, S. Zalzal, S. Clair, A. Sarkissian, D. F. Perepichka, J. D. Wuest, F. Rosei and A. Nanci, *Small*, 2009, 5, 996-1006). Studies have shown that surface modifications profoundly influence almost all tested cellular activities from cell polarization and migration to gene expression profile, differentiation, and apoptosis (K. Kandere-Grzybowska, C. J. Campbell, G. Mahmud, Y. Komarova, S. Soh and B. A. Grzybowski, *Soft Matter*, 2007, 3, 672-679; K. Kulangara and K. W. Leong, *Soft Matter*, 2009, 5, 4072-4076; V. Brunetti, G. Maiorano, L. Rizzello, B. Sorce, S. Sabella, R. Cingolani and P. P. Pompa, *Proc Natl Acad Sci USA*, 2010, 107, 6264-6269; M. J. Dalby, N. Gadegaard, R. Tare, A. Andar, M. O. Riehle, P. Herzyk, C. D. Wilkinson and R. O. Oreffo, *Nat Mater*, 2007, 6, 997-1003; J. Z. Gasiorowski, S. J. Liliensiek, P. Russell, D. A. Stephan, P. F. Nealey and C. J. Murphy, *Biomaterials*, 2010, 31, 8882-8888). However, these studies followed only phenomenological approaches due to the lack of knowledge of the underlying biochemical mechanism. While some insights were provided by works investigating the role of focal adhesion maturation during contact guidance, the effects of topography on cell-to-substrate interaction prior to spreading are still unknown. Fundamental questions remain to be answered, such as whether onset of spreading and contact guidance are independently modulated by the surface topography and whether it is possible to decouple the two processes by pure topographical means.

Thus, beside the tremendous development of stent technology in the last 20 years, there are still some major difficulties which have to be overcome:

Drug eluting stents (DES) are coated with drugs that are gradually released from the stent after implantation and inhibit cell growth. This will reduce significantly the renewed narrowing of the treated vessel, a process known as restenosis. The disadvantage of DES, however is, that they have increased thrombogenicity at blood exposed parts of the incomplete covered stent struts. This so called late stent thrombosis (LST) often proves fatal also after years of implantation and patients have to take blood thinners such as clopidogrel, which renders the treatment very expensive.

Bare metal stents (BMS) are used to unblock occluded arteries and provide a mechanical support to keep the treated vessel open. Normally they show an anti-thrombogenic surface modification and are not coated with active drugs. Thus they are not associated to the same degree with the problem of LST. However, the disadvantage of BMS is, they do not offer any protection against renewed narrowing of the treated vessel, which occurs in 20-30% of all is cases after BMS implantation. This is because after vessel wall injury during stent deployment smooth muscle cells (SMC) inside the arterial wall proliferate much faster than endothelial cells resulting in the formation of neointimal tissue. As a consequence, patients are more likely to undergo repeated surgery to re-open the treated vessel.

Stents with surface microstructures are just under research investigation and no clinical data from human are known today. U.S. Pat. No. 6,190,404 B1 describes for the first time the usage of microgrooves on stent struts for faster healing after stent deployment by favorably modifying endothelial cell (EC) migration. However, these patterns are not optimized for EC migration, proliferation or adhesion, differentiation of circulating precursor cells under flow conditions, whereas it is known that wall shear stress in combination with certain micropattern can have profound effects on cellular behaviour during adhesion, differentiation, migration and proliferation.

Moreover other structural design elements like pits and holes in different geometrical arrangements (square, hexagonal, disordered, different heights) were not mentioned in this application but may also play a pivotal role in the development of a functional EC layer (ECL). A similar approach is described in US 2005/0209684 A1.

The intention of this invention with respect to the case wherein the implant is a stent is therefore to provide a specific geometrical arrangement of surface structures in the submicron to micrometer regime for faster re-endothelialization of stent struts after drug eluting stent deployment via Percutaneous Coronary Intervention (PCI). This soft healing approach will significantly reduce the problem of late stent thrombosis (LST) and restenosis.

SUMMARY

In order to solve or at least to reduce one or more of the above mentioned technical problems, there is provided an implant with a surface layer having a topographic modification including a line pattern with ridge and groove widths of 0.9 to 1.1 µm, more preferred 0.95 to 1.05 µm, especially 1 µm, and a ridge height of more than 0.9 µm, especially 1 µm or more.

As a result of the inventive topographic modification, neointima formation on the surface of an implant could be significantly accelerated. The adhesion of for example Human Umbilical Vein Endothelial Cells (HUVEC) is supported by the inventive surface structure. The topographic modification includes a line pattern (or grating) of characteristic dimension suitable for cell adhesion. Ridge width and groove width should be the same or nearly the same (for example a ratio of 0.9 µm ridge width to 1.1 µm groove width should be included). The entire surface or only fractions of the surface of the implant may be covered by the surface layer showing the inventive topographic modification.

According to a preferred embodiment, the implant includes a main body made of a metallic material and the surface layer is disposed on the main body and being made of a polymer material. The manufacturing process of the inventive topographic modification can be simplified for example in that a surface layer of the polymeric material is heated up to its glass transition temperature and a die having a negative contour of the line pattern is pressed into the polymeric material.

Preferably, the metallic material is a biodegradable metallic material. The biodegradable metallic material may be one selected of a magnesium alloy, iron alloy, magnesium or iron. Especially, the biodegradable metallic material is a magnesium alloy. A magnesium alloy is to be understood as a metallic structure, the main component of which is magnesium. The main component is the alloy component that has the highest proportion of weight in the alloy. The share of the main component preferably amounts to more than 50% by weight, particularly more than 70%. The same applies to what is understood of the term iron alloy.

For purposes of the present disclosure, a material referred to as biodegradable in which degradation occurs in a physiological environment, which finally results in the entire implant or the part of the implant formed by the material losing its mechanical integrity. Artificial plasma, as has been previously described according to EN ISO 10993-15:2000 for biodegradation assays (composition NaCl 6.8 g/l. $CaCl_2$ 0.2 g/l. KCl 0.4 g/l. $MgSO_4$ 0.1 g/l. $NaHCO_3$ 2.2 g/l. $Na_2HPO_4$ 0.126 g/l. $NaH_2PO_4$ 0.026 g/l), is used as a testing medium for testing the corrosion behavior of a material coming into consideration. For this purpose, a sample of the material to be assayed is stored in a closed sample container with a defined quantity of the testing medium at 37° C. At time intervals-tailored to the corrosion behaviour to be expected of a few hours up to multiple months, the sample is removed and examined for corrosion traces in a known way.

In addition, also the polymer material of the surface layer may a biodegradable polymer material. Exemplary biodegradable polymers include polydioxanone, polyglycolide, polycaprolactone, polylactide (for example poly-L-lactide, poly-D,L-lactide and copolymers and blends such as poly(L-lactide-coglycolide), poly(D,L-lactide-coglycolide), poly(L-lactide-co-D,L-lactide), poly(L-lactide-cotrimethylene carbonate), polysaccharides (for example chitosan, levan, hyaluronic acid, heparin, dextran, cellulose), polyhydroxyvalerate, ethylvinyl acetate, polyethylene oxide, polyphosphoryl choline, fibrin, albumin, polyhydroxybutyric acid (atactic, isotactic, syndiotactic and blends thereof), and the like.

The line pattern of the surface layer may be covered by a biodegradable topcoat. The topcoat may protect the line pattern as well as a drug eluting coating especially during the process of implantation.

According to another preferred embodiment of the invention, an angle between a groove bottom surface and a side wall of the ridge is between 90° to 135°.

The line pattern needs not to cover the whole surface of the implant but may be interrupted for example in longitudinal extension of the implant. According to own investigations (cf. FIG. 15), this deterioration of microstructures will not have any significant effect on cell orientation and migration until more than 40% of the lines and spacing are missing. At 60% loss of structure integrity cells behave as on flat surfaces. In other words, the line pattern is preferably perfect or is deteriorated to less than 40% of the perfect line pattern. Furthermore, the implant may include two or more areas of line pattern, wherein for example the orientation of the line pattern with respect to a longitudinal extension of the implant is different. Preferably, the line pattern is oriented orthogonal to implant geometry. In case of the implant is a stent, the line pattern is preferably oriented orthogonal to a stent strut direction.

Implants are devices introduced into the body via a surgical method and comprise sensors, fasteners for bones, such as screws, plates, or nails, surgical suture material, intestinal clamps, vascular clips, prostheses in the area of the hard and soft tissue, and anchoring elements for electrodes, in particular, of pacemakers or defibrillators.

The implant is preferably a stent. Stents are endovascular prostheses which may be used for treatment of stenoses (vascular occlusions). Stents typically have a hollow cylindrical or tubular basic mesh which is open at both of the longitudinal ends of the tubes. The tubular basic mesh of such an endoprosthesis is inserted into the blood vessel to be treated and serves to support the vessel. Stents of typical construction have filigree support structures made of metallic struts which are initially provided in an unexpanded state for introduction into the body and are then widened into an expanded state at the location of application. Preferably, the line pattern covers at least a luminal surface of the stent.

As described above, arterial walls are injured during the deployment of BMS. In 20-30% of all cases, SMC proliferation is enhanced over EC growth due to an inflammatory response that leads to a non-functional ECL and excessive tissue formation. To prevent this, the wound healing process should be reasonable fast supporting EC growth while suppressing SMC proliferation. Development of a functional endothelial cell layer covering the stent and therefore shielding the thrombogenic metal surface from direct blood contact will minimize LST, Restenosis on the other hand will be suppressed by the reduced inflammatory response to stent implantation by providing a functional ECL. Beside external chemical or biological signaling pathways, topography in the nano to micro-meter range does also influence ECL formation. The reason behind is, cellular mechanosensation is influencing adhesion, proliferation and migration by transducing the external mechanical signals into internal biological stimuli regulating cellular behaviour. By precisely control the geometrical dimensions, the orientation and arrangement of the structural features and the wall shear stress along the strut surface one can significantly enhance and accelerate the wound healing process. Not only circulating progenitor cell adhesion may be enhanced but also proliferation and migration of existing endothelial cells will be influenced and guided by the micro-texture.

The stent may be a drug eluting stent (DES). Incorporation of drug eluting stents into a vessel is usually prohibited or inhibited by use of antiproliferative drugs like rapamycin or paclitaxel as a side effect. However, formation of a thin neointima appears to be essential for healing of the vessel. By means of the inventive topographic modification the healing process can be supported and accelerated.

According to the studies for the present invention, live-cell imaging and high-resolution microscopy has been applied to measure spreading dynamics and contact guidance on biocompatible structured substrates. The interaction between cells and topography was further resolved using scanning electron microscopy. Additionally, specific inhibitors of cell contractility to further analyze the role of the ROCK1/2-myosin-II pathway in the regulation of onset of endothelial spreading and contact guidance has been used. Finally, biochemical techniques and fluorescent staining to pinpoint the relevant molecular players contributing to this effect is have been applied.

DETAILED DESCRIPTION

Materials and Methods

Substrate Fabrication

Figure 9A:
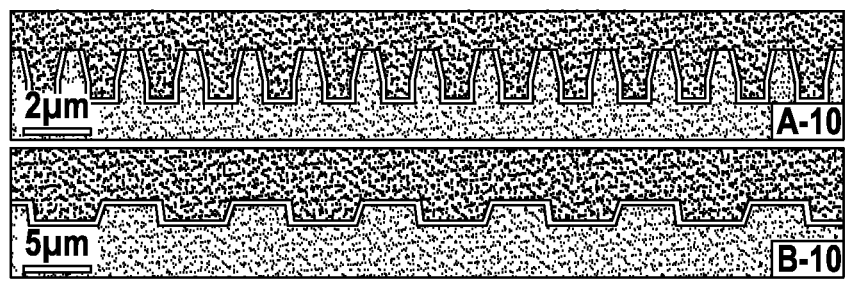
FIG. 9 Fabrication process of COC-gratings.
Figure 9B:
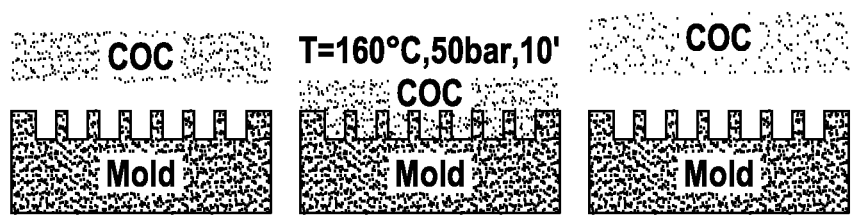
Figure 9C:
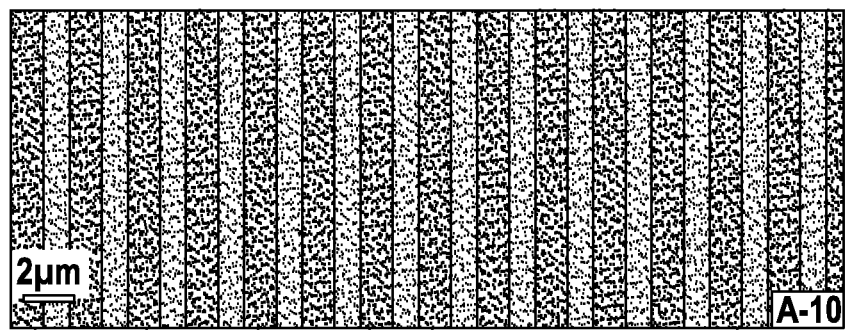

For the fabrication of the molding tool, chromium patterns had to be transferred into a 525 µm thick silicon wafer via photo lithography and reactive ion etching. In the first step the wafer was spin-coated with a Microposit 51805 positive tone photo resist (thickness ~0.5 µm). The gratings were imprinted on 180 µm thick untreated Cyclic Olefin Copolymer (COC) foils (Ibidi, Germany) using nanoimprint lithography (NIL). The height of the ridges was adjusted by tuning the etching time while the side wall steepness was kept constant. This procedure generated squared patterned areas of 1 cm side length. Ten molds were fabricated with ridge and groove widths of 1 µm and ridge height of 0.1, 0.2, 0.4, 0.6, 0.8, 1, 1.5, and 2 µm and with ridge and groove width of 5 µm and ridge height of 0.1 and 1 µm (Table 1). The COC substrates were placed on top of the mold and softened by raising the temperature up to 160-180° C. A pressure of 50 bar was then applied for 10 minutes before cooling down to 40° C. Finally, the pressure was released and the mold was detached from the substrate with a scalpel (FIG. 9). Samples were then treated with oxygen plasma (100 W for 30 seconds) to increase the hydrophilicity of the surface and to promote cell adhesion. The water static contact angle of COC before treatment was 94.3°±0.4° and was reduced to 27.8°±1.3° after treatment. The imprinted gratings were systematically characterized by scanning-electron microscopy before cell culturing (FIG. 9).

Figure 13:
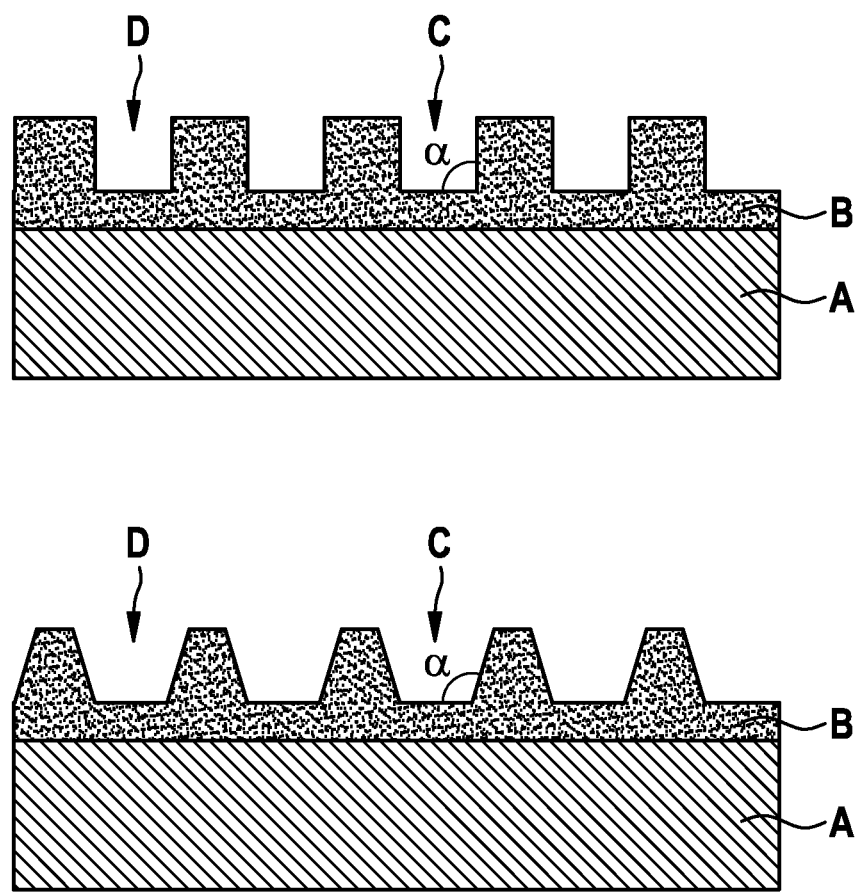
FIG. 13 Sectional views of the line patterns.

FIG. 13 is a schematic sectional view of the line pattern according to two embodiments of the invention. The implant body A (for example a stent) is covered by a surface layer B (for example a drug eluting polymer layer). An angle α between the bottom of a groove D and a side wall of the ridge C is set to be 90° in the upper embodiment and more than 90° in the lower embodiment.

TABLE 1

| grating | ridge width (µm) | groove width (µm) | groove depth (µm) |
|---|---|---|---|
| FLAT | 0 | 0 | 0 |
| A-20 | 1 | 1 | 2 |
| A-15 | 1 | 1 | 1.5 |
| A-10 | 1 | 1 | 1 |
| A-8 | 1 | 1 | 0.8 |
| A-6 | 1 | 1 | 0.6 |
| A-4 | 1 | 1 | 0.4 |
| A-2 | 1 | 1 | 0.2 |
| A-1 | 1 | 1 | 0.1 |
| B-10 | 5 | 5 | 1 |
| B-1 | 5 | 5 | 0.1 |

Constructs

Vinculin-FP635 (Far Red Fluorescent Protein) construct was used (a kind gift of Dr. Ralf Kemkemer, Max Planck Institute for Metals Research, Stuttgart, Germany).

Antibodies

Rabbit anti-Src (pan; #2123), FAK (pan; #3285), phospho-Src (#2101) and phospho-FAK (#3283) were purchased from Cell Signaling Technology (USA). Goat anti-VE-Cadherin (#6458) was purchased from Santa Cruz Biotechnology Inc. (USA). Secondary goat anti-rabbit HRP (#65-6120) and donkey anti-goat (A-11055) antibodies were from Invitrogen (Carlsbad, USA).

Cell Culture and Inhibitor Treatment

Human umbilical vein endothelial cells (HUVEC; Invitrogen) were grown in medium 200PRF supplemented with fetal bovine serum 2% v/v, hydrocortisone 1 μg/ml, human epidermal growth factor 10 ng/ml, basic fibroblast growth factor 3 ng/ml and heparin 10 μg/ml (all reagents from Invitrogen) and were maintained at 37° C. and 5% $CO_2$. To visualize focal adhesions, HUVEC were transfected using a Neon Transfection System (Invitrogen). All reported experiments were performed using cells with less than seven passages in vitro. Up to six imprinted COC substrates (1 $cm^2$) were individually sealed to the bottom of a well in a 12-multiwell culture plate (Becton Dickinson, USA) hereafter denoted as 'topographic chip'. The topographic chips were sterilized by overnight treatment with ethanol and rinsed three times with PBS. The substrates were then coated with Poly-L-lysine (PLL) solution 0.01% (Sigma-Aldrich, USA) according to the manufacturer's specification. The topographic chip was stored at 4° C. until the seeding of the cells.

To generate confluent monolayers cells were seeded on COC substrates at high density (60-70×$10^4$ cell/$cm^2$) as reported by Lampugnani et al. and cultured for three days. To measure the time to onset of spreading, cells were detached from a subconfluent cell culture and resuspended in pre-warmed medium without antibiotics. The cells were then counted, diluted to reach a concentration of 5×$10^4$ cells in 1 ml of medium and then seeded onto the substrates.

To measure the spreading dynamics of individual HUVECs contacting flat or topographically modified substrates, the cell membrane was labelled using a vital fluorophore (CellTracker Green, C2925 Molecular Probes; Invitrogen). HUVECs were seeded 24 hours before the experiment in a 12 well plate (1×$10^5$ cell/well). For staining, cells were washed and incubated for 30 min at 37° C. in medium without serum containing 0.5 μM CellTracker Green. After labeling, complete fresh medium was added and cells were left to recover for 30 minutes before starting the spreading experiment. Cells were gently detached, counted and seeded on the substrate and imaging started immediately after seeding.

For contractility inhibition experiments during endothelial spreading, the cells were treated with DMSO (corresponding v/v), 30 μM ML-7, 10 μM Y27632 or 50 μM blebbistatin. The drugs were dissolved in DMSO (ML-7, blebbistatin) or in distilled water (Y27632) and added to the cells 30 minutes before starting the experiment.

Immunostaining

HUVEC adhering to COC substrates were fixed for 15 minutes with 3% paraformaldehyde (PFA, pH=7.4) at room temperature. Cells were then rinsed once with PBS and permeabilized for 30 minutes with a solution of 0.1% TritonX-100 in PBS at room temperature. After rinsing with PBS, cells were incubated for 3 hours in blocking buffer. F-actin was stained by incubating with TRITC-phalloidin (Sigma, USA) overnight at 4° C. After rinsing five times with PBS, the substrates were mounted on glass coverslips and immediately imaged. VE-Cadherin and phosphorylated (p)-FAK in HUVECs were localized following the protocol reported by Lampugnani et al. 22 Briefly, cells were fixed for 15 minutes with 3% PFA and then permeabilized for 3 minutes with a solution of 0.1% TritonX-100 in 3% PFA at room temperature. After washing once with PBS, cells were incubated for 1 hour with blocking buffer. Samples were then incubated with primary antibody in blocking buffer overnight. After five washings with 5% BSA in PBS, cells were incubated with secondary antibody for 1 hour. Samples were finally washed three times (1 hour each) in PBS, post-fixed for 2 minutes in 3% PFA and mounted with DAPI-containing Vectashield (Vector Labs Inc., USA).

Wide Field Time-Lapse Microscopy

Cell imaging was performed using an inverted Nikon-Ti wide-field microscope (Nikon, Jaw pan) equipped with an Orca R-2 CCD camera (Hamamatsu Photonics, Japan). After cell seeding, the topographic chip was placed under the microscope in an incubated chamber (Life Imaging Services, Switzerland), where temperature and $CO_2$ concentration were maintained at 37° C. and 5%, respectively. Images were collected with a 20×, 0.45 NA long-distance objective (Plan Fluor, Nikon). Endothelial spreading on topographic substrates in topographic chips was recorded in parallel time-lapse movies for up to 6 different substrates (a flat control and five different gratings). Before starting the experiment, five non-overlapping positions were chosen within each substrate and stored in a position list. Immediately after cell seeding, the experiment was started to automatically acquire a differential interference contrast (DIC) image at each saved position with a time resolution of 1 minute for a total of one or two hours. Focal drift during the experiments was eliminated using the microscope's PFS autofocus system. At the end of the experiment, the resulting time-lapses were converted into a single 8 bit movie for each imaging field under analysis.

Fluorescent movies of CellTracker Green-labelled cells were collected at the cell-substrate interface using a 40×, 1.30 NA oil immersion objective (PlanFluor, Nikon) for a total of one or two hours. Images were collected in both DIC and FITC channels with a time resolution of 1 or 2 minutes.

Fluorescent images of HUVEC expressing vinculin-FRFP or stained with TRITC-phalloidin, VE-Cadherin, or pFAK antibodies were acquired with a 60×, 1.2 NA water immersion objective (PlanApo, Nikon) using a TRITC or FITC filter.

Scanning Electron Microscopy (SEM)

One hour after seeding, cells were fixed with 2.5% glutaraldeyde (Sigma) in sodium cacodylate buffer (pH 7.2, 0.15 M) for 1 hour and successively rinsed three times with sodium cacodylate buffer. 23 Samples were then dehydrated and dried with ethanol absolute at increasing concentrations (50%, 70%, and 98%) and coated with a 20 nm thick gold layer by thermal evaporation. The metal layer was shorted to the SEM sample holder to allow proper electron discharge during imaging. The substrates were then loaded into a LEO 1525 (Carl Zeiss Inc., Germany) field emission SEM and image acquisition was carried out by secondary-electron detection with an Everheart-Thornley detector in order to enhance the topography of cell substrate interfaces.

Image Analysis

Collected movies were loaded into ImageJ (National Institutes of Health, USA) and analyzed as follows: In a first step, movies acquired on patterned substrates were filtered by Fast Fourier Transform (FFT). This procedure eliminates the scattering generated by the gratings. The time to onset of spreading on the respective substrates was then measured for each cell detected within all parallel time-lapses acquired. The time to onset of spreading was individuated by the first frame of the time-lapse (_t=1 minute) in which the cell produces visible membrane protrusions at the cell-substrate-interface. A mean time to onset of spreading was calculated for each substrate under analysis by averaging the values measured for all individual cells. HUVEC alignment to the gratings was measured for all cells detected in the last frame of each recorded movie. The cell profile was manually drawn using the 'Freehand selection' tool of ImageJ. The cell area and the cell orientation angle were then obtained respectively using the 'Area' and the 'Fit ellipse' options in the 'Measurements' tool of ImageJ. In the latter case, the obtained value in degrees was normalized relative to the orientation of the grating extracted from the same image. The range of possible alignment angles between cells and gratings is 0° to 90°. Thus a value close to 0° indicates perfect alignment while a value of 45° indicates no alignment.

For the measurements of spreading dynamics, collected fluorescent movies were loaded into ImageJ and the cell profile at the cell-to-substrate interface was manually drawn using the 'Freehand selection' tool of ImageJ. The cell area and the cell circularity were then obtained respectively using the 'Area' and the 'Circularity' options in the 'Measurements' tool of ImageJ. The quantitative comparison of spreading dynamics in cells interacting with different substrates was performed by analyzing the central and more active time of spreading during which cells increase their area from 20% to 80% of their eventual maximum area, as reported by Dubin-Thaler et al.

For focal adhesion size measurements, fluorescent images of HUVEC transiently expressing vinculin-FP635 were loaded into ImageJ and the profile of each visible focal adhesion was manually drawn using the "Freehand selection" tool. A value for the focal adhesions size (in $\mu m^2$) was obtained using the "Measurements" tool. For groove bridging efficiency quantification, SEM images were loaded into ImageJ. The total number of grooves encompassed by the cell as well as the number of membrane arcs bridging over a groove was manually counted for each cell.

Western Blot

For western blot analysis, nine COC surfaces were assembled into a square and surrounded by a Polydimethylsiloxane (PDMS) barrier to create an artificial incubation chamber with an active surface of approximately 9 $cm^2$. After sterilization with ethanol, freshly detached HUVEC (120, 000) were seeded onto these artificial wells. After 20 minutes of incubation, medium was removed and lysis buffer was directly added. Lysed cells were then collected by scraping. Cell lysates were analyzed by standard Western blot using antibodies against total FAK and Src proteins and their phosphorylated isoforms. Unsaturated bands on Amersham ECL-Hyperfilms (GE Healthcare, UK) were analyzed using a calibrated densitometer (GS-800, Bio-Rad, USA) and Quantity One software version 4.5.0 (Bio-Rad). Band intensity was quantified using global background subtraction and the 'Volume Analysis' tool of Quantity One.

Statistical Analysis

Statistical comparison of average time to onset of spreading and average alignment obtained on different gratings and on control flat substrates was performed using a non-parametric Mann-Whitney test ($\alpha=0.05$). All quantitative measurements reported are expressed as average values±the standard error of the mean. The total number of events counted is reported in the upper or lower right corner of the presented graphs.

Results

Experimental Setting

In order to prove the biocompatibility of substrates under analysis, the ability of human umbilical vein endothelial cells (HUVEC) to generate a differentiated monolayer on cyclicolefincopolymer (COC) foils was initially assessed. HUVECs proved perfectly viable on all tested substrates and generated a confluent monolayer within 3 days of culture when seeded at high density. These monolayers showed a typical localization of the junctional marker vascular endothelial (VE)-Cadherin at cell-cell contacts, confirming their full differentiation.

Figure 1A:
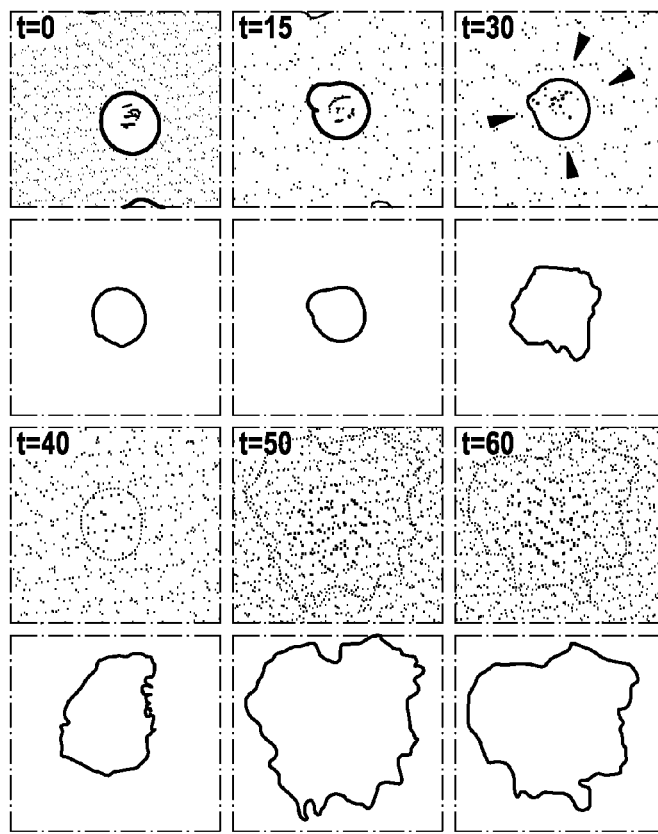
FIG. 1 Endothelial spreading on COC substrates.
Figure 1B:
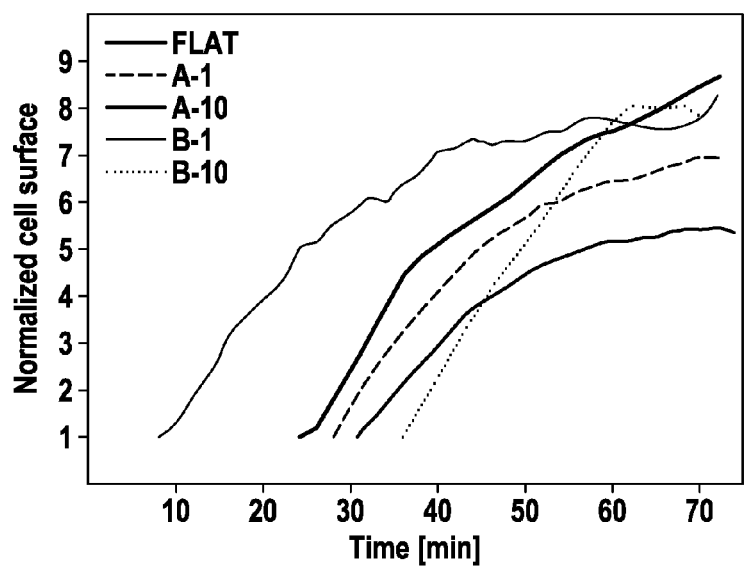

FIG. 1 shows the dynamics of endothelial spreading on COC substrates. Shortly after seeding, individual HUVEC in contact with the substrate are round and display no visible membrane protrusions at the cell-to-substrate interface (t=0 and t=15 minutes; FIG. 1A). Onset of spreading is individuated by the generation of visible membrane protrusions (t=30 minutes; FIG. 1A) typically appearing with fast dynamics. Subsequently, further membrane protrusions are produced, leading to rapid cell spreading on the surface (FIG. 1A).

In order to investigate the influence of substrate topography on endothelial cell spreading, the projected cell surface was recorded during the entire process for individual cells contacting four different grating types (A-10, A-1, B-10, B-1; Table 1) and compared to what was observed on flat substrates. The graph in FIG. 1B reports individual measurements of spreading dynamics for cells contacting different substrates. In all tested conditions, the projected surface increases after onset of spreading in a process corresponding to rapid cell spreading and eventually reaches a plateau which is then maintained by the cells. Importantly, the time to onset of spreading varies considerably among cells contacting different substrates (FIG. 1B) suggesting that the substrate topography plays a critical role during the early phases of endothelial spreading.

Endothelial Spreading on Textured Surfaces

In order to quantify the effect of surface texture on endothelial spreading, the time to onset of spreading and the final orientation of cells on gratings were measured and compared to those obtained on flat substrates under otherwise identical experimental conditions (FIG. 2). The graph in FIG. 2A reports the average time to onset of spreading of HUVEC onto four different grating types (A-10, A-1, B-10, B-1; Table 1). Comparison with the average time to onset of spreading on flat substrates reveals that the gratings with the smallest tested lateral periodicity and deepest tested grooves (A-10) accelerates onset of spreading by about 40% (FIG. 2A). On all other tested gratings, onset of spreading is disfavored. The negative effect results in a relative delay ranging from 21% (B-10) to 49% (B-1). These results demonstrate that substrate topography significantly modulates early cell-substrate-interaction, either promoting or demoting the onset of spreading. Additionally, these results indicate that among gratings with the same lateral feature size, endothelial cells initiate spreading earlier on substrates with to deeper grooves (FIG. 2A).

Figure 2A:
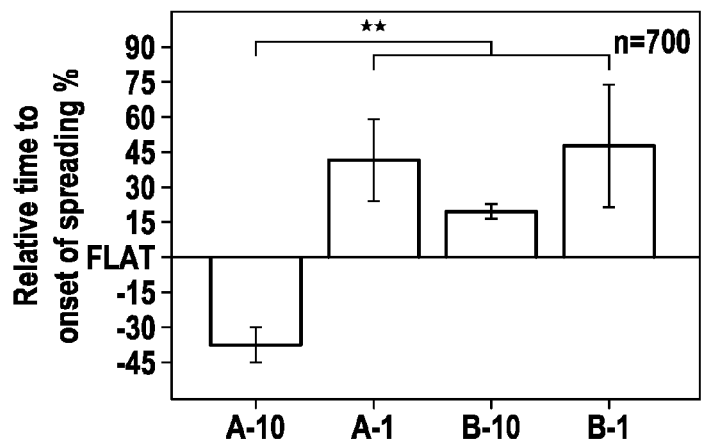
FIG. 2 Time to onset of spreading and cell alignment to different gratings.
Figure 2B:
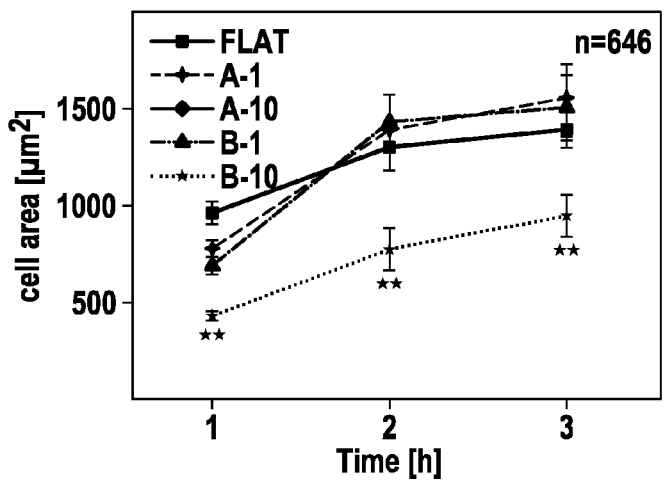

In order to further evaluate endothelial regeneration on the textured substrates, the cell area was quantified at different times after seeding and compared to what was measured in the case of cells contacting flat substrates (FIG. 2B). One hour after seeding, HUVECs contacting flat substrates show an average projected cell surface of 955±58 $\mu m^2$. At this time point, the projected surface of cells seeded on textured substrates ranges from 772±40 $\mu m^2$ for cells on gratings A-1 to 420±21 $\mu m^2$ for cells on gratings B-10. However, cells on gratings A-1, A-10 and B-1 spread to values comparable to the control within two hours after seeding and maintain similar values at later time points (3 hours, FIG. 2B). Notably, at 2 and 3 hours after seeding, the cells spreading on gratings B-10 are 40% and 30% smaller than control, respectively, indicating that on this specific topography cell spreading is partially impaired (FIG. 2B).

Figure 2C:
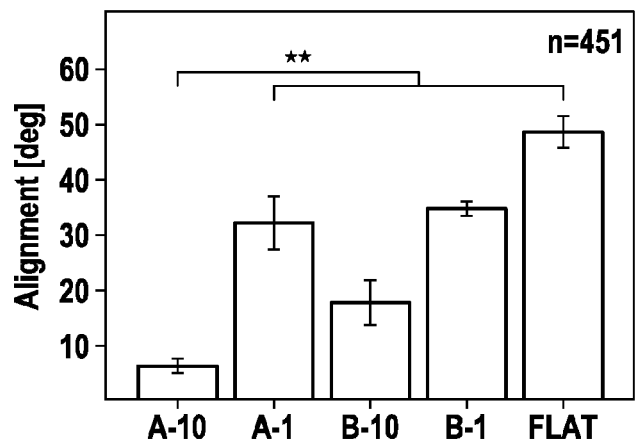
Figure 2D:
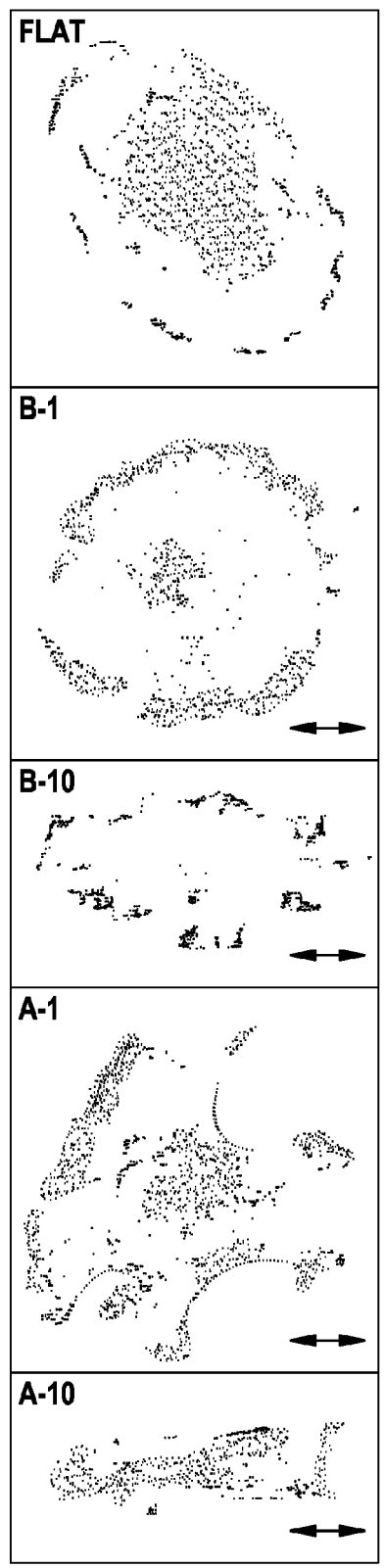

Anisotropic topographies are known to induce the polarization of adherent cells. 16 Contact guidance measures the efficiency of cell-topography-interaction upon spreading. The average cell-to-substrate alignment angles are 6.3±1.3°, 32.5±5°, 18±4.3°, and 34.9±1.3° for substrates A-10, A-1, B-10, and B-1, respectively (FIG. 2B). Altogether, these results demonstrate that, to a different extent, endothelial cells polarize along the direction of gratings on all tested patterns. However, contact guidance efficiency is significantly higher on gratings with deeper grooves (A-10 and B-10). Interestingly, the topography that accelerates onset of spreading (A-10) also proves to be the most efficient in inducing cell alignment along the gratings. The distribution of microfilaments in HUVEC adhering to gratings and to flat substrates further reveals the resulting cellular polarization (FIG. 2C). As expected, cells interacting with substrates A-10 and B-10 display visible stress fibers which are highly aligned to the grating direction, while cells interacting with gratings A-1 and B-1 are similar to ones on flat substrates. Here, filamentous actin concentrates in lamellipodia and in randomly oriented fibers (FIG. 2C).

Figure 11:
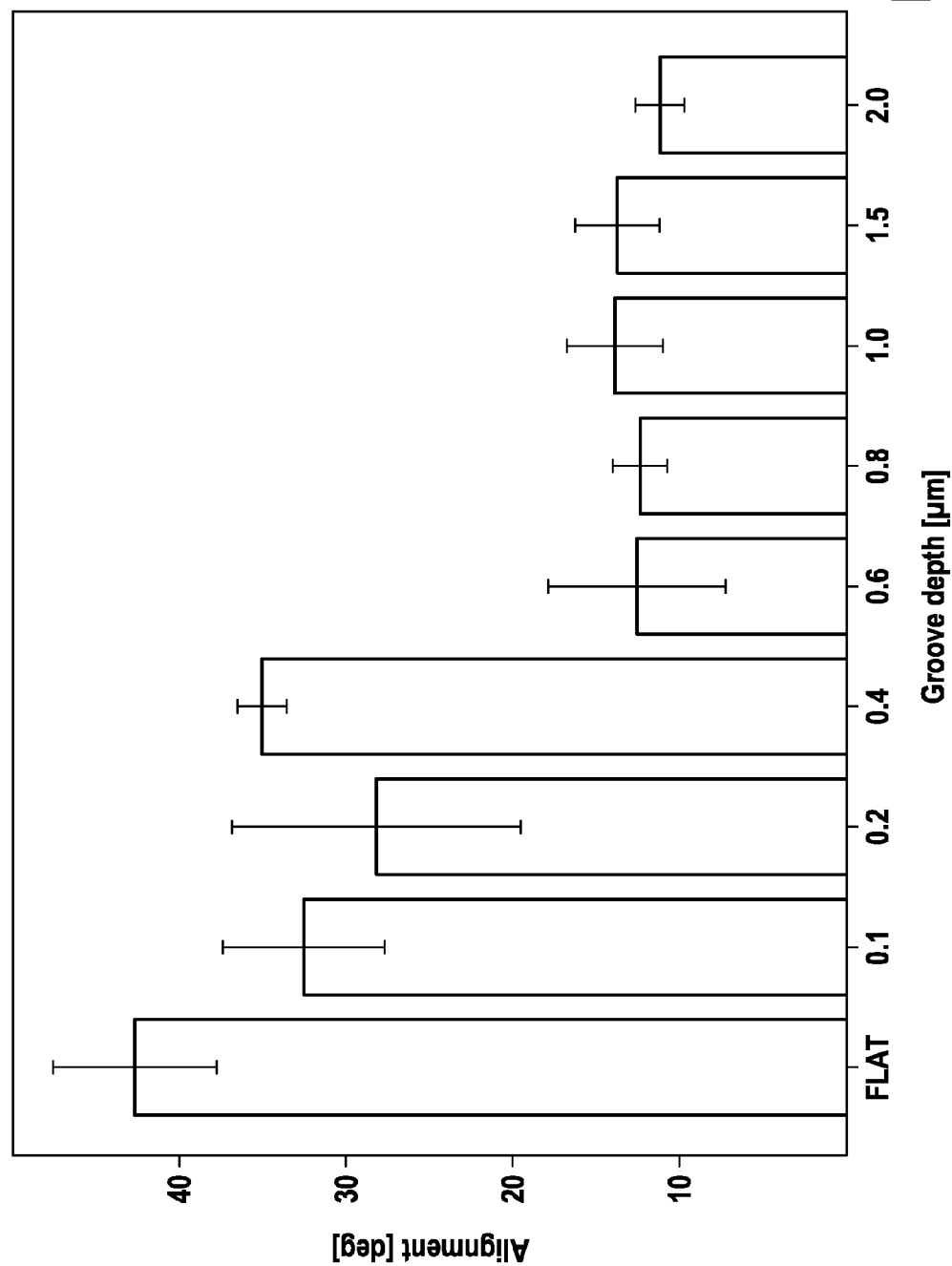
FIG. 11 Influence of groove depth on cell polarization.

It could be further demonstrated that polarization of the cells along a centre line of the structure is not influenced by the groove depth (FIG. 11). As could be seen, a groove depth of at least 1 μm is preferred and deeper structures do not have any significant influence on cell polarization.

Figure 12:
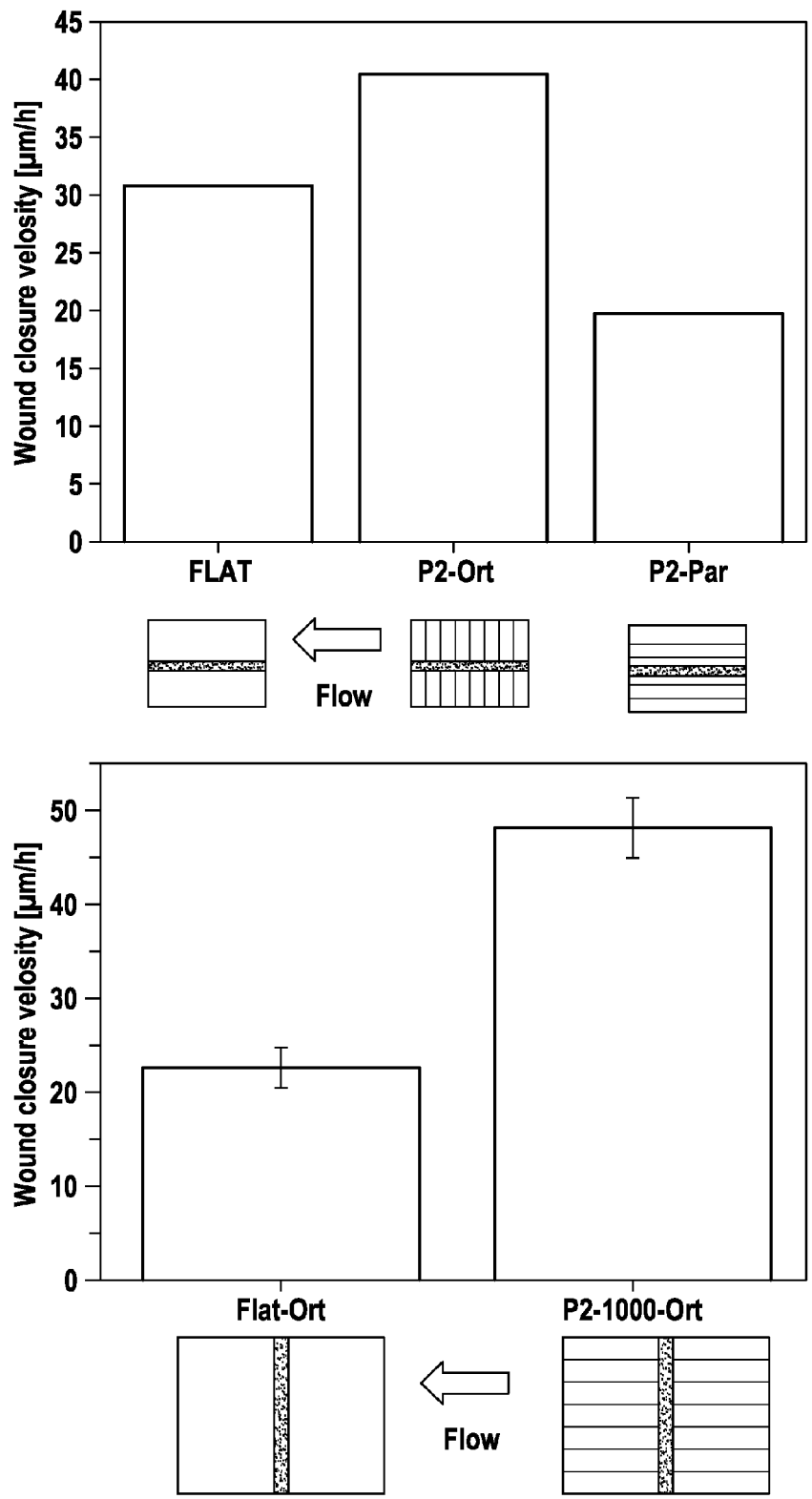
FIG. 12 Velocity of wound closure under a simulated blood flow.
Figure 14:
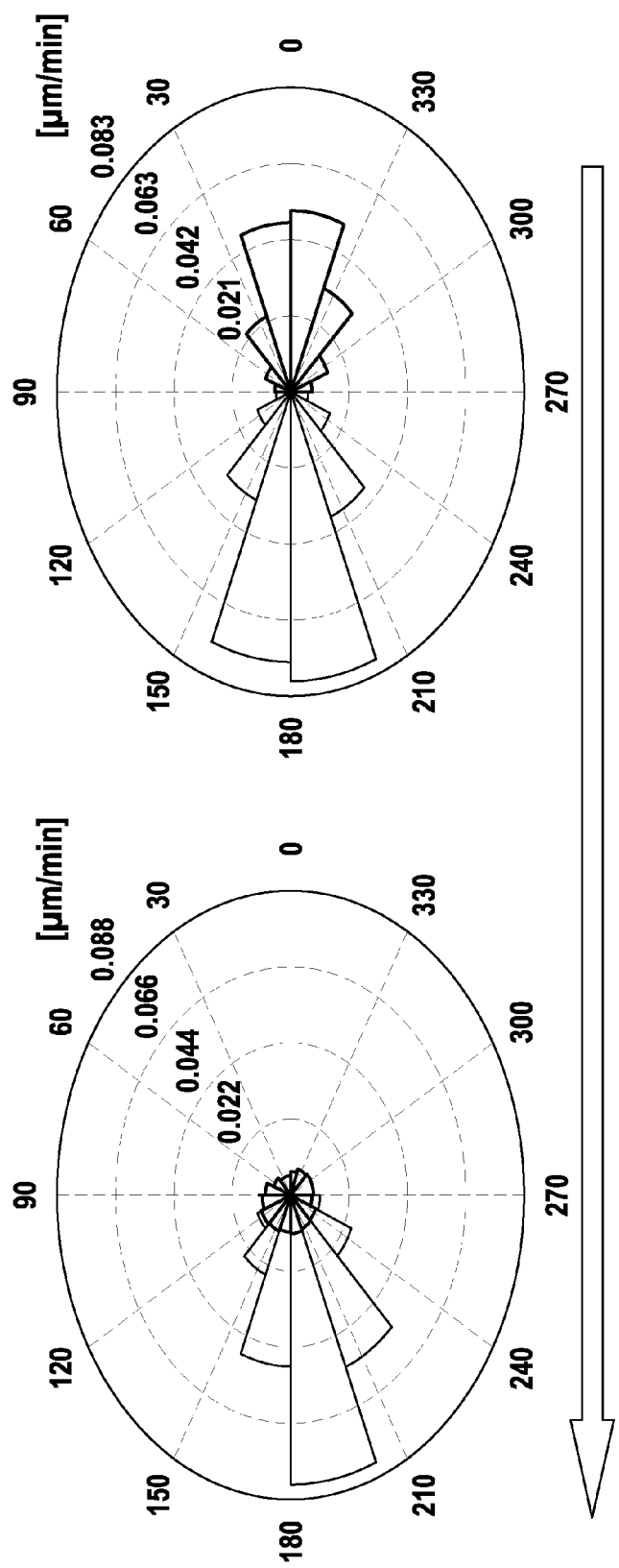
FIG. 14 Velocity and migration orientation of the cells located at the edge of a wound.
Figure 15A:
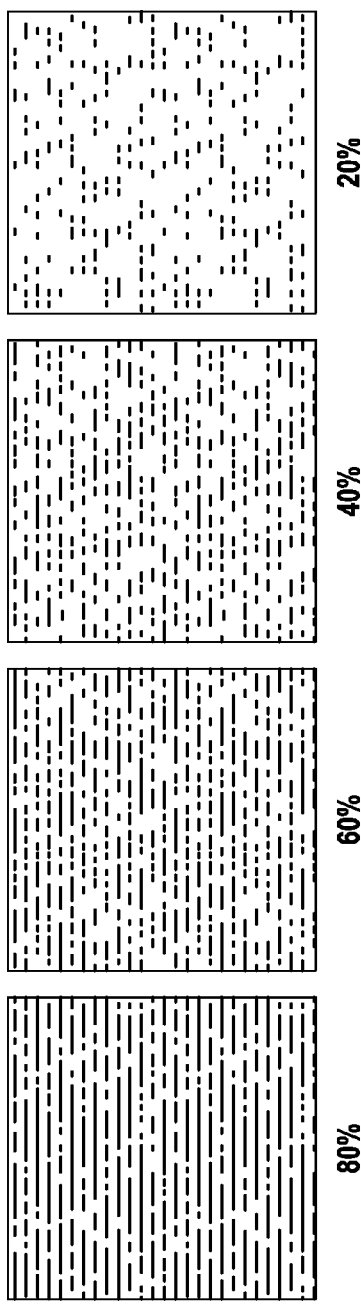
FIG. 15 Average alignment angle of endothelial cells on line structures deteriorated by 20%, 40%, 60% and 80% compared to flat and not deteriorated lines.
Figure 15B:
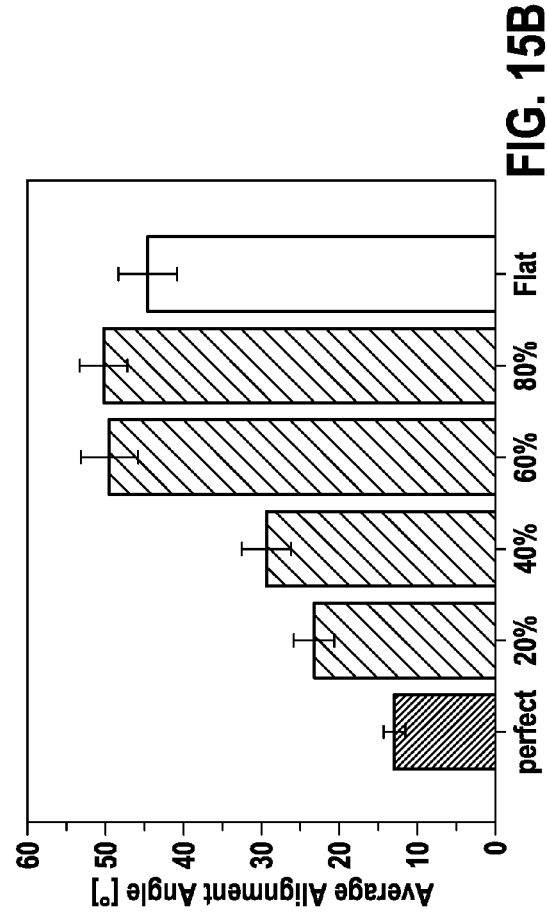

Furthermore, the velocity of wound closure under a simulated blood flow has been studied. It could be demonstrated that a vertical alignment of the grooves and ridges with respect to the blood flow reverses the direction of migration of the cells located at the downstream edge of the wound against the flow. This reversal significant accelerates wound closure as compared to cells grown on non-structured surfaces, where the cell migration of the downstream wound edge is in direction of flow (FIG. 12 and FIG. 14). The broad line in the centre of the structures illustrates the position of the wound.

In FIG. 14 the solid lines represents the radial distribution of the velocity vector of cells located at the downstream edge of the wound and the dashed lines the radial distribution of the velocity vector of cells located on the upstream edge of the wound. There is no difference in migration direction and velocity of cells located upstream between flat surfaces (left) and structured surfaces (right) under simulated blood flow. However, the direction of migration of cells located at the downstream edge is reversed and directed against the flow. The black arrow in FIG. 14 illustrate the direction of simulated blood flow.

FIG. 12 furthermore shows that the relative orientation of line structures, blood flow and wound have a significant impact on wound healing velocity. The highest wound healing velocity is obtained with a wound aligned orthogonal to the direction of blood flow and line structures aligned orthogonal to the wound. Nevertheless a comparable wound healing velocity is obtained in the situation where the wound is aligned parallel to the direction of blood flow and the line structures are aligned orthogonal to the wound. What must be avoided is the situation where wound and line structures are parallel to each other. Optimal in-growth, i.e. endothelialisation of implants is therefore obtained when implant geometry and line structures are orientated orthogonal to each other. A technical solution for stent implants would be to align the line structure orthogonal to the direction of the struts at each point of the stent body. This can be for example easily achieved by a structuring tool adapted to the specific stent design.

Spreading Dynamics on Gratings A-10

Figure 3A:
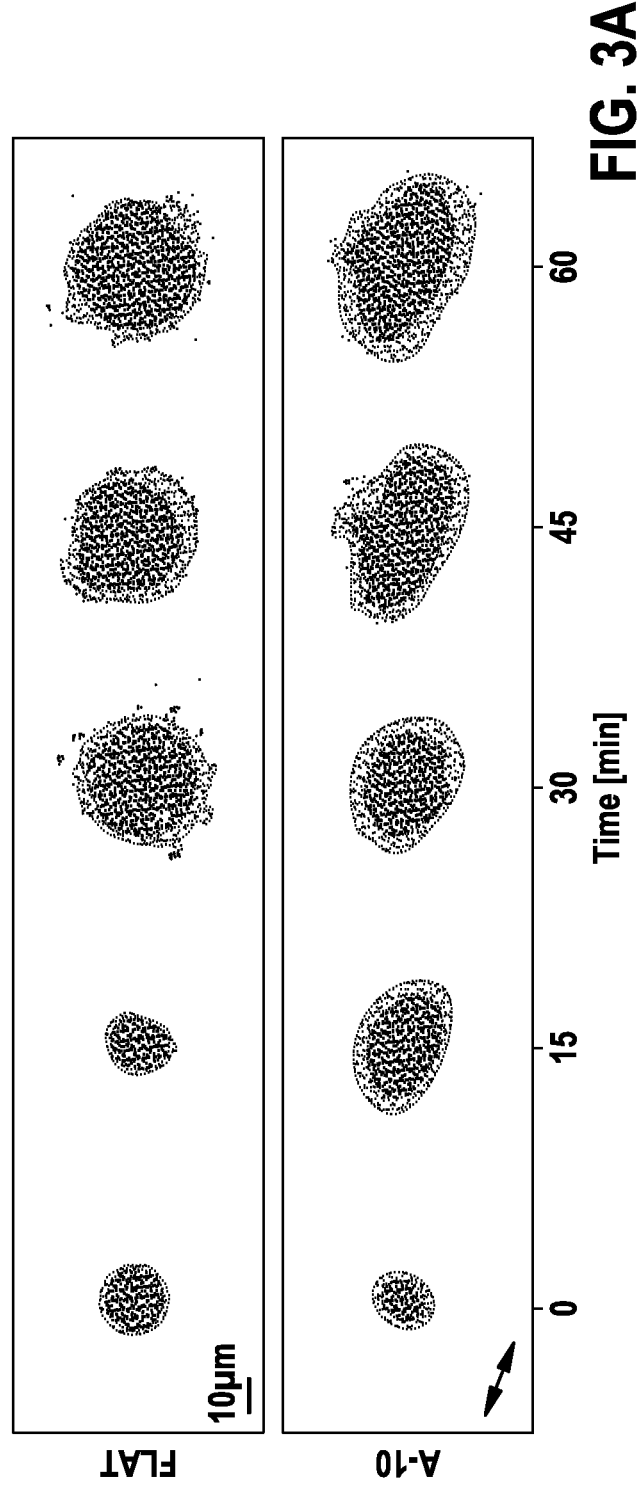
FIG. 3 Dynamics of endothelial spreading and circularity on gratings.

In order to better understand the effect of surface topography during endothelial spreading, we performed a high-resolution analysis of cells surface and shape dynamics (FIG. 3). FIG. 3A shows the cell surface evolution over the entire spreading process in representative cells contacting flat substrates or gratings A-10. While the cell contacting a flat substrate shows visible membrane protrusions 30 minutes after seeding and spreads conserving a circular shape (t=45 and 60 minutes), the cell interacting with gratings A-10 initiates spreading in less than 15 minutes and rapidly polarizes by the generation of membrane protrusions predominantly along the grating direction (t=30, 45 and 60 minutes).

Figure 3B:
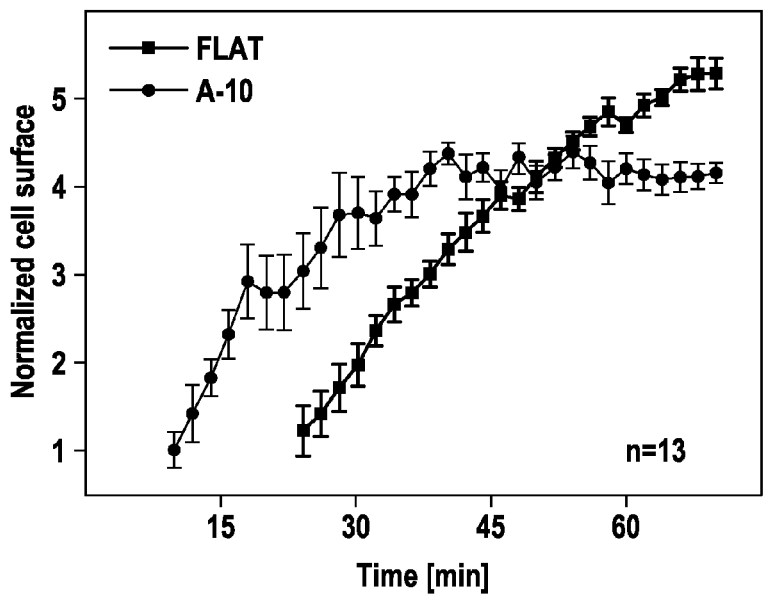
Figure 3C:
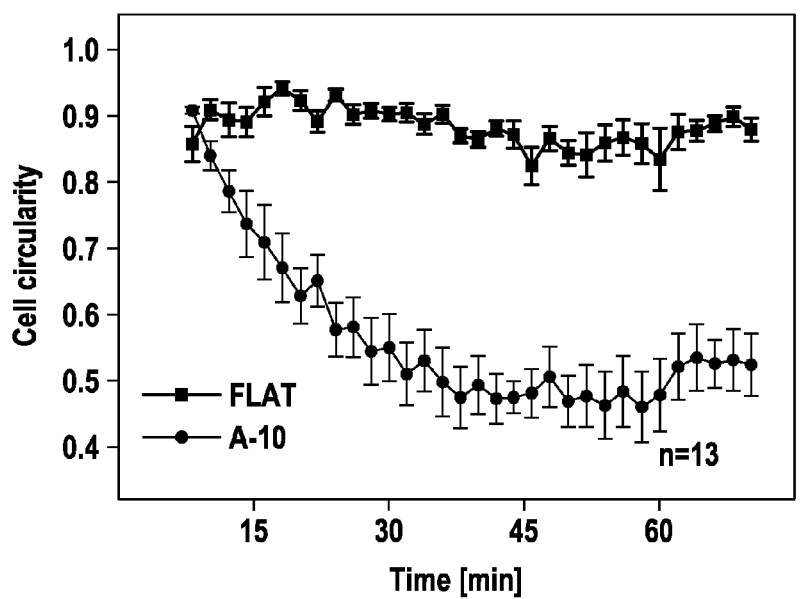

The graph in FIG. 3B reports the temporal evolution of average projected surface for cells contacting flat substrates or gratings A-10. HUVECs on gratings A-10 initiate spreading on average 8±2 minutes after seeding. In this condition, the projected cell surface increases 4.2 fold within 30-35 minutes after seeding and is then maintained for the rest of the recording. Differently, cells contacting a flat substrate initiate spreading 24±2 minutes after seeding and experience a fivefold increase of their projected cell surface within 65 minutes after seeding. However, the rates of increase in contact area of cells contacting gratings A-10 are not significantly different than those of cells contacting flat substrates (86.2±14.1 and 61.5±9.8 μm²/min, respectively; p=0.2). The graph in FIG. 3C reports the corresponding circularity for cells spreading on gratings A-10 or on flat substrates. Prior to onset of spreading, cells on both substrates show similar shape and display circularity close to 1. Importantly, while cells contacting flat substrates maintain a rather circular shape along the entire process of spreading, the interaction with gratings A-10 induces a dramatic cell-shape change immediately after onset of spreading. On this substrate, the circularity rapidly drops to a plateau close to 0.5 which is then maintained after full spreading. Altogether these results indicate that the major effect of gratings A-10 is via the reduction of the time to onset of spreading and trough the polarization of cell protrusions rather than through a change in the spreading velocity.

Effect of Groove Depth

Figure 4A:
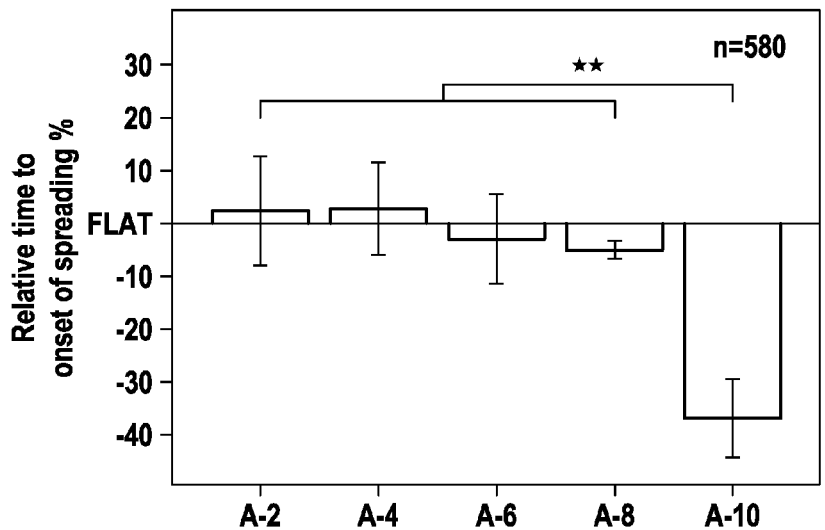
FIG. 4 Influence of the groove depth on time to onset of spreading and alignment of endothelial cells.
Figure 4B:
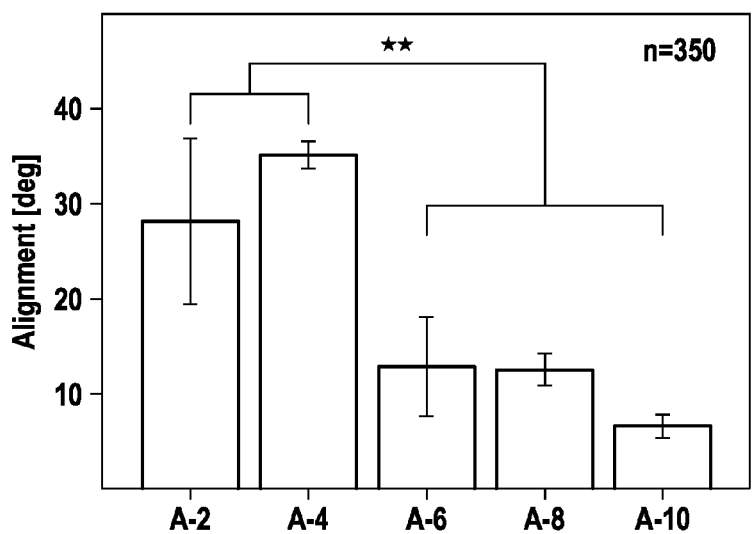
Figure 10A:
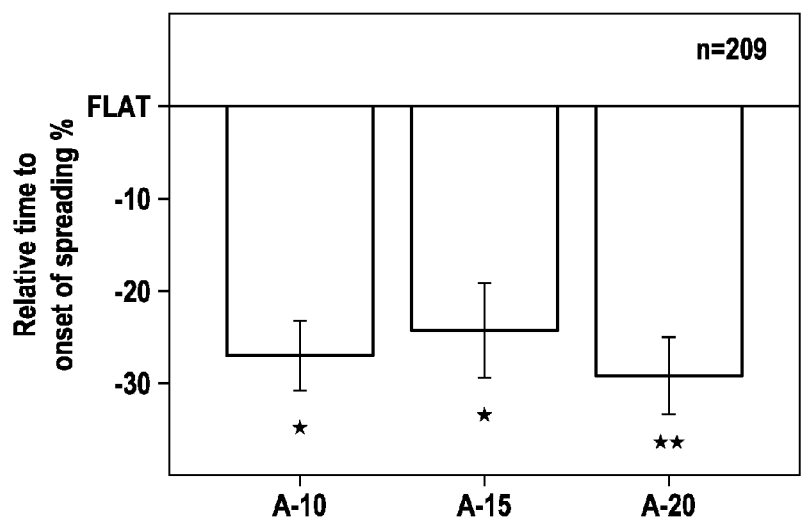
FIG. 10 Time to onset of spreading and cell alignment to different gratings.
Figure 10B:
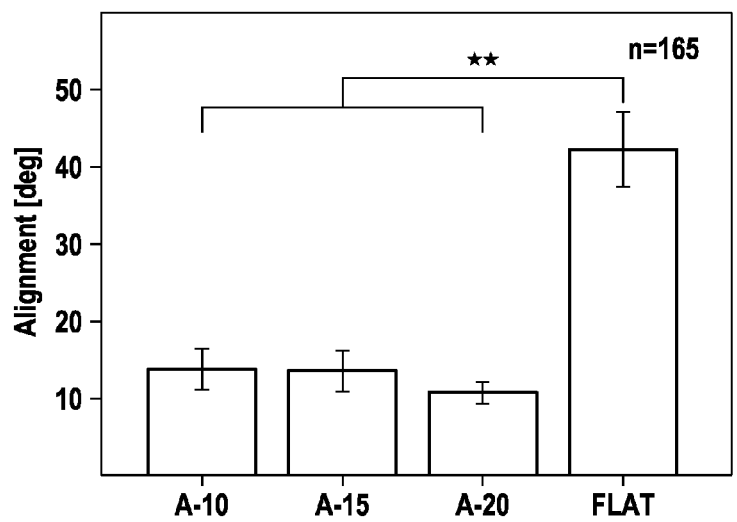

In order to decouple the contribution of groove depth to the effect of substrate A-10 on onset of spreading and contact guidance, five gratings with the same lateral period but increasing groove depths (A-2, A-4, A-6, A-8, A-10, A-15, and A-20; Table 1) were tested (FIG. 4 and FIG. 10). Endothelial cells initiate spreading with similar dynamics on shallow gratings (groove depths up to 0.6 μm) and control flat substrates (FIG. 4A). A small enhancement is seen on 0.8 μm deep gratings (A-8; FIG. 4A) while full enhancement is measured on gratings with groove depths of 1 μm or deeper (FIG. 4A). Interestingly, the measure of cell alignment (FIG. 4B) individuates two different levels of efficiency in contact guidance: Cells contacting gratings with groove depth of 0.2 and 0.4 μm align significantly worse than cells adhering to to gratings with deeper grooves (FIG. 4B). Altogether, these results indicate that the measured effects on onset of spreading and contact guidance are differently sensitive to groove depth. While acceleration of spreading onset starts at groove depth of 0.8 μm, the threshold at which contact guidance efficiency increases is found at a depth of 0.6 μM.

Figure 4C:
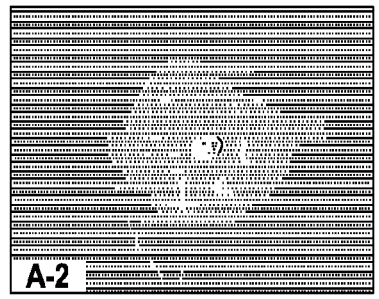
Figure 4D:
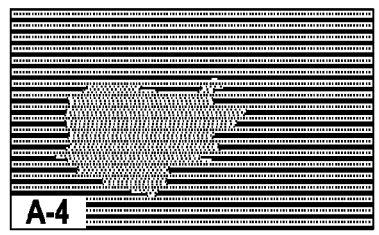
Figure 4E:
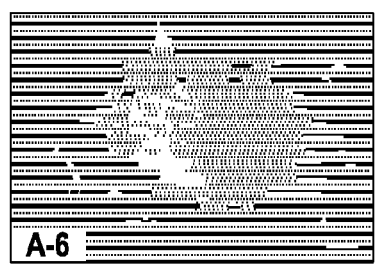
Figure 4F:
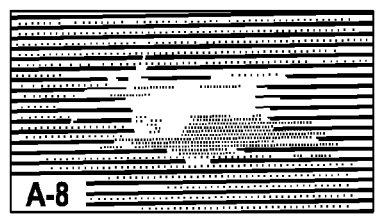
Figure 4G:
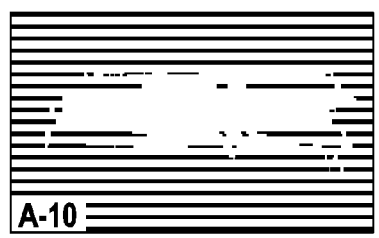
Figure 4H:
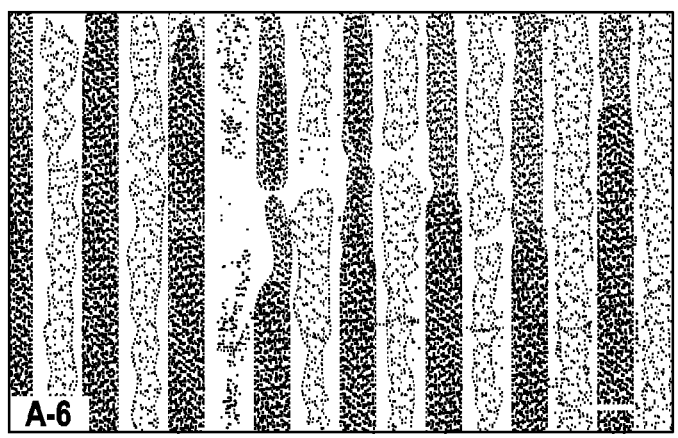
Figure 4I:
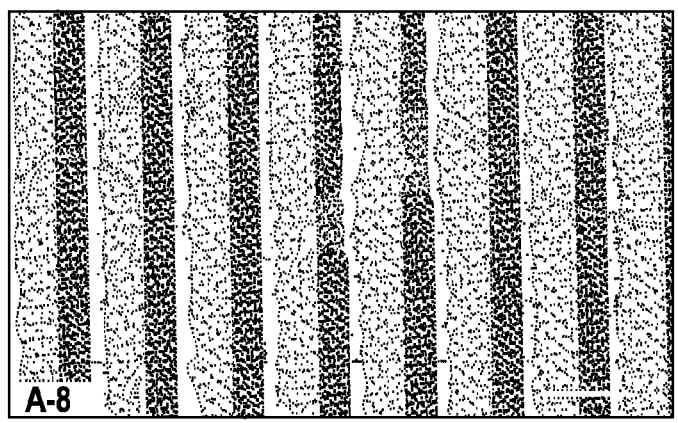
Figure 4L:
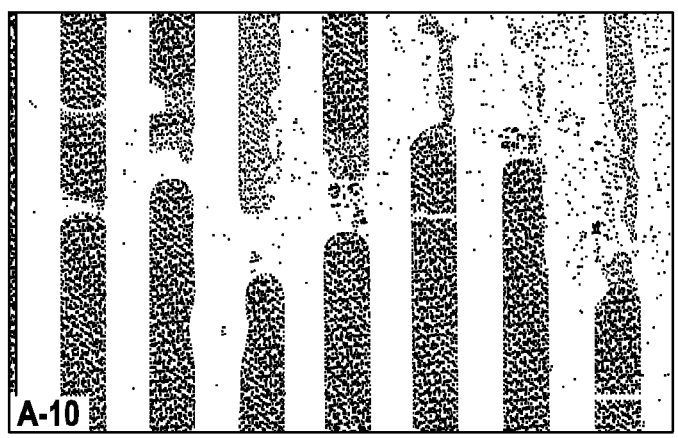

Scanning electron microscopy images of HUVEC spreading on gratings with lateral period of 2 μm and groove depths ranging from 0.2 to 1 μm (FIGS. 4C-G and Table 1) confirm an increased orientation of cells along gratings with deeper grooves. Importantly, while on shallower gratings (A-2, A-4, A-6, and A-8; FIGS. 4C-E) the cell body and membrane protrusions clearly contact the bottom of the grooves (FIG. 4H) and rarely bridge from one ridge to the next (FIG. 4I), endothelial cells adhering to gratings with deeper grooves are positioned exclusively on ridges (FIG. 4G) and produce membrane arcs bridging over the grooves. Importantly, onsets of spreading and contact guidance are favored on topographies limiting cell-to-substrate interaction to the ridges, thus forcing the clustering of adhesion in geometrically constrained regions. As we demonstrated previously, this confinement can modulate focal adhesion maturation along the grating and thus favor contact guidance.

Focal Adhesion Maturation and Cell-Mediated Contractility

Figure 5A:
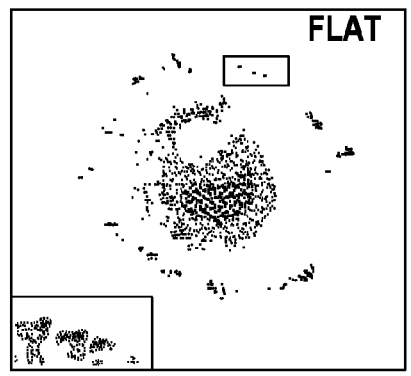
FIG. 5 Focal adhesion maturation on spreading-enhancing topography.
Figure 5B:
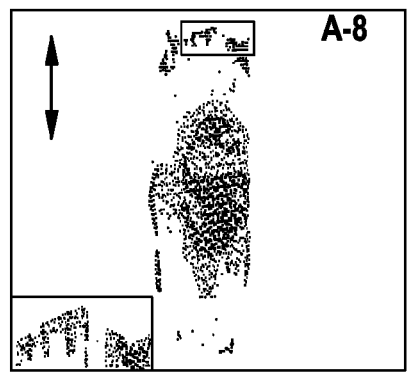
Figure 5C:
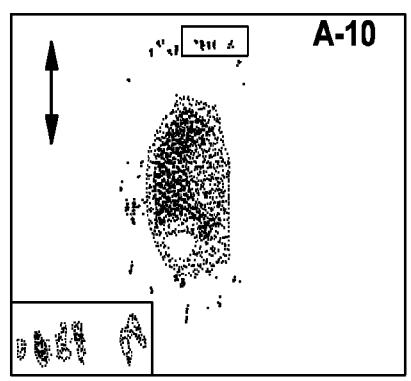
Figure 5D:
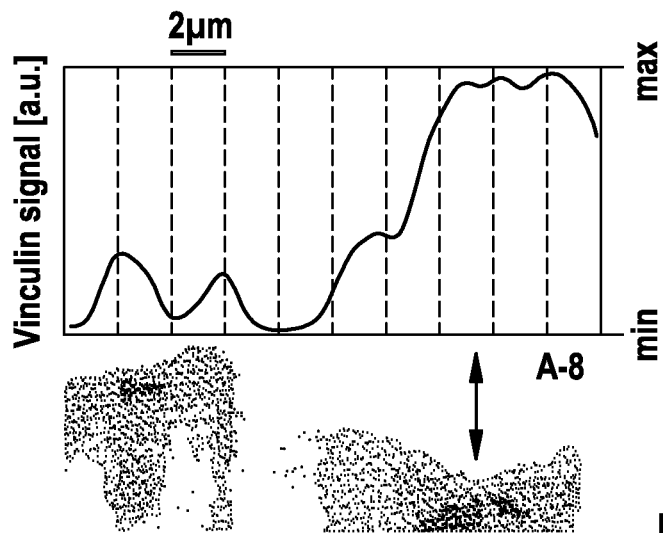
Figure 5E:
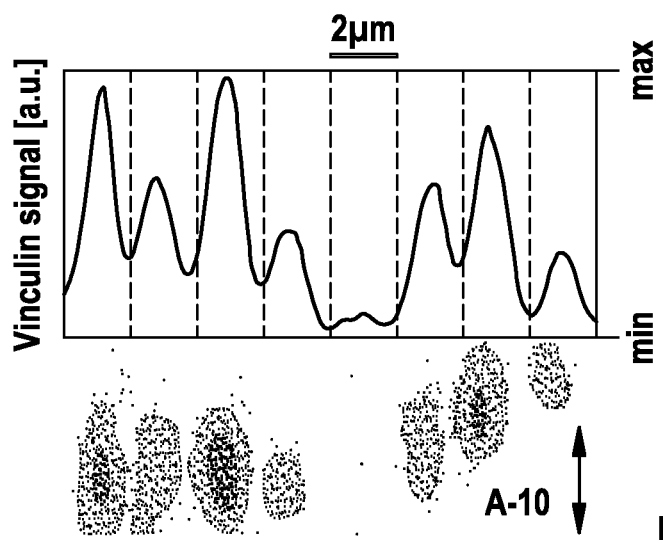
Figure 5F:
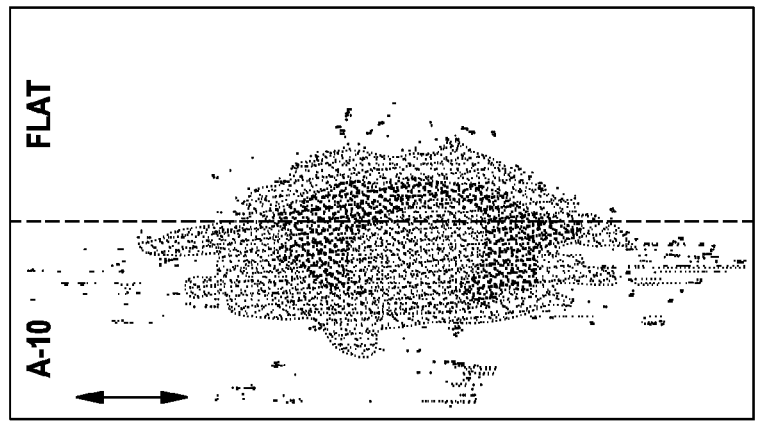
Figure 5G:
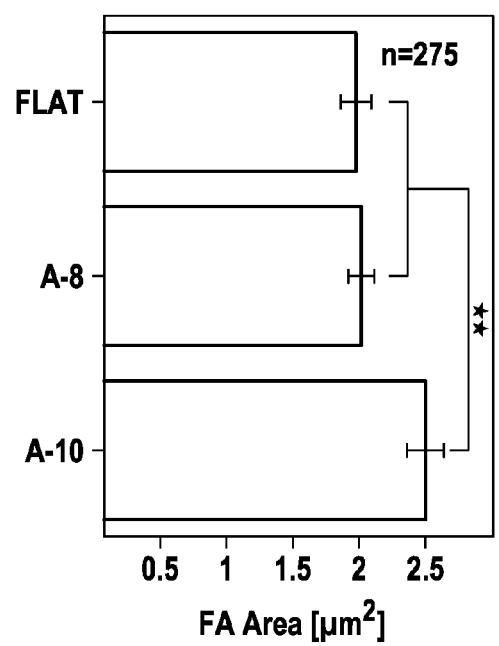

To elucidate the mechanism of interaction between endothelial cells and grating A-10 (FIGS. 2-4), we analyzed the establishment and maturation of integrin-based adhesions. Both initial focal complexes and mature focal adhesions were visualized by transient expression of vinculin-FP635 in endothelial cells. Under our experimental conditions, overexpression of vinculin did not affect endothelial adhesion and spreading as reported by others. After spreading, vinculin-rich structures are revealed as discrete bright regions at the cell-to-substrate interface (FIG. 5). Vinculin-rich adhesions established by endothelial cells on flat substrates are randomly distributed along the cell periphery (FIG. 5A). Importantly, when contacting gratings A-10, the vinculin-rich adhesions are visibly elongated along the gratings and confined to ridges (FIG. 5C). Owing to the resulting geometrical constraint, only adhesions growing along the grating direction are able to mature, while the maturation of adhesions growing in other directions is limited by the grooves (FIG. 5E). In addition, the size of adhesions established by cells on gratings A-10 is significantly larger ($2.3\pm0.1$ $\mu m^2$; FIGS. 5 D-E) than on control flat substrates ($1.8\pm0.1$ $\mu m^2$), indicating that confinement onto ridges promotes the maturation of aligned adhesions. Focal adhesion constraint and improved maturation are only detected in to HUVECs spreading on gratings with groove depth of 1 $\mu m$. On slightly shallower gratings (A-8; FIG. 5B) the vinculin signal freely crosses both ridges and grooves (FIG. 5D) and the average FA size is similar to that measured on flat substrates ($1.9\pm0.1$ $\mu m^2$; FIG. 5G). These results correlate well with the groove bridging efficiency revealed by SEM images and demonstrate that the FAs established by endothelial cells upon spreading on gratings A-10 are confined to the top of the ridges and mature faster than those generated by cells contacting shallower gratings or flat substrates.

Adhesion maturation requires forces generated by the cell and the mechanical linkage between the actin cytoskeleton and the adhesion site, which are established after the onset of spreading. Hence, the question is whether the measured effect on FA maturation (FIG. 5) is necessary to accelerate the onset of spreading and/or enhance contact guidance on gratings A10 (FIGS. 2-4).

Figure 6A:
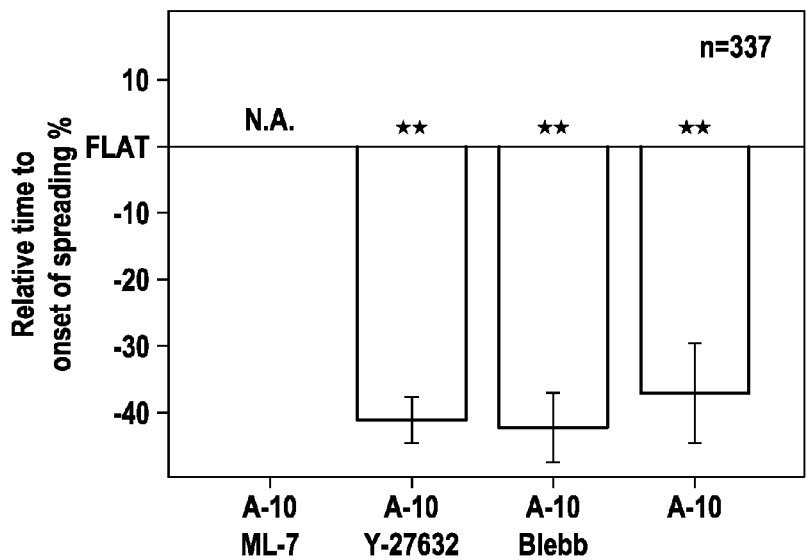
FIG. 6 ROCK1/2 and myosin-II activities are required for contact guidance but dispensable for initial endothelial spreading.
Figure 6B:
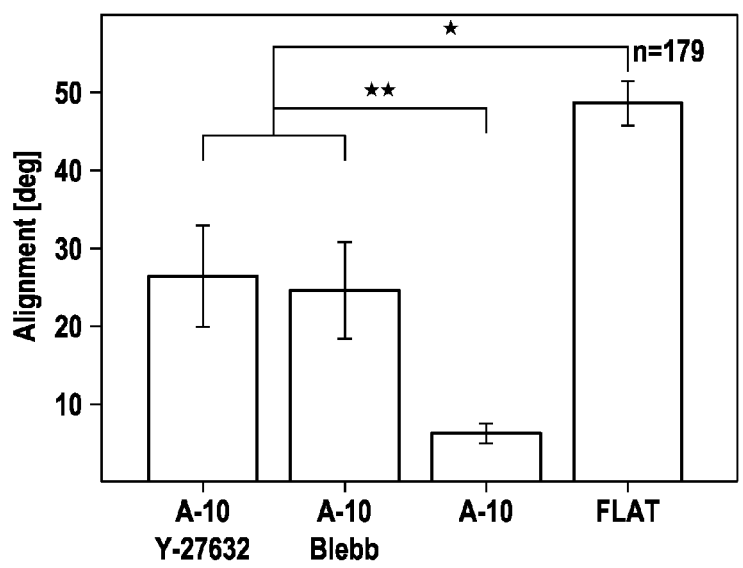
Figure 6C:
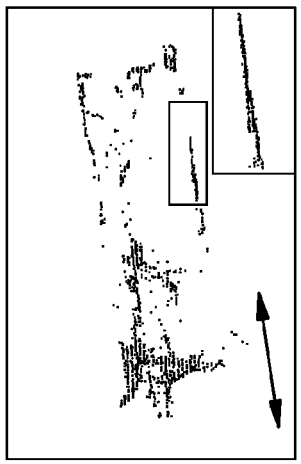
Figure 6C:
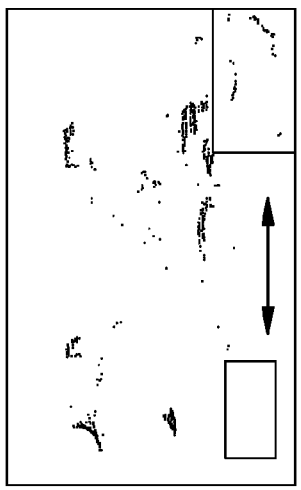
Figure 6C:
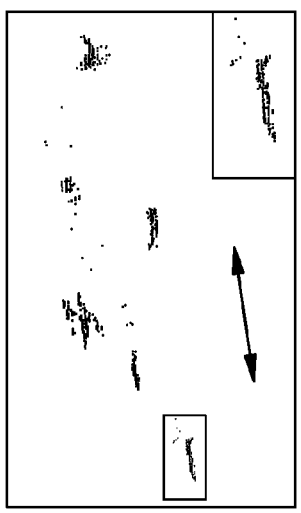

To answer this, FA maturation was blocked by the direct inhibition of myosin-II mediated contractility with Blebbistatin or by the selective inhibition of its two major activator kinases (FIG. 6): Rho-dependent kinases 1/2 (ROCK1/2) with Y27632 and myosin light chain kinase (MLCK) with ML7.4, Inhibition of myosin-II or of ROCK1/2 activity has no effect on the time to onset of spreading for HUVEC interacting with gratings A-10 (FIG. 6A). Interestingly, inhibition of MLCK completely ablates HUVEC spreading (FIG. 6A). Inhibition of myosin-II mediated cell contractility has, on the contrary, a dramatic effect on contact guidance (FIG. 6B) and thus on the actin cytoskeleton of the treated cells (FIG. 6C). Endothelial cells treated with Blebbistatin or with Y27632 spread in a similar manner as the untreated controls, but align significantly worse to gratings A-10 (average alignment $26.5\pm6.5°$ and $24.7\pm6.4°$; respectively; FIG. 6B). In these cells, the stress fibers are visibly loose and their orientation along the gratings is compromised (FIG. 6C). Altogether, these results demonstrate that ROCK1/2 and myosin-II mediated contractility is dispensable for the acceleration of the onset of spreading, while it is necessary for the later-stage contact guidance effect.

Integrin Signaling

Figure 7A:
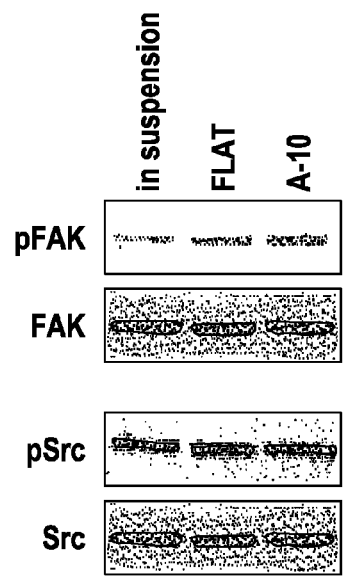
FIG. 7 Biochemical analysis of integrin signaling on spreading-enhancing topography.
Figure 7B:
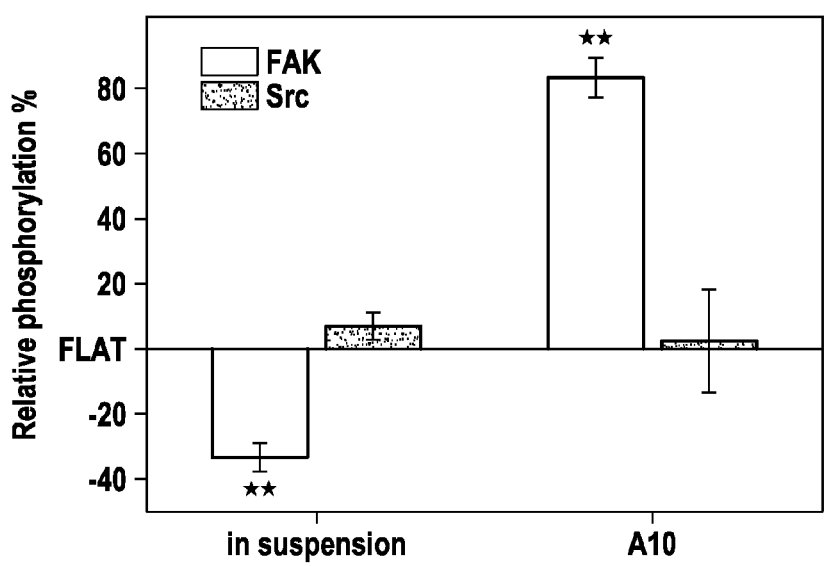
Figure 7C:
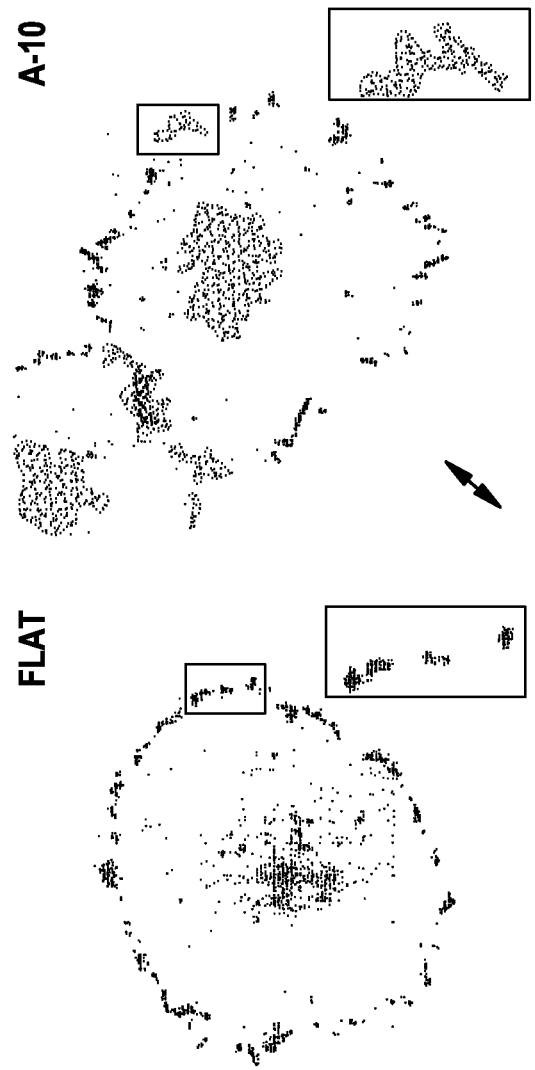

Finally, we performed a biochemical analysis of the observed effect of gratings A-10 (FIG. 2) by examining the phosphorylation signals (i.e. the activation state) of two major mediators of integrin signaling: FAK and Src-kinase. FAK is recruited to initial integrin adhesion sites and auto-phosphorylated at Tyr397 (pFAK; FIG. 7). Additional recruitment of auto-phosphorylated Src (Tyr416, pSrc) leads to the activation of downstream targets and results in FA maturation. In endothelial cells interacting with gratings A-10, the pFAK signal is increased by $83.7\pm6.3\%$ when compared to control cells spreading on a flat substrate (FIG. 7B). This result is further confirmed by the localization of pFAK signal in cells spreading on gratings A-10 or on flat substrates (FIG. 7C). Accordingly, cells kept in suspension for 20 minutes show a reduction of $33.5\pm4.2\%$ in pFAK compared to control cells (FIG. 7B). However, no significant change is detected in pSrc levels for cells kept in suspension or seeded on grating A10 ($7.46\pm4.3\%$ and $3.3\pm15.9\%$; respectively). These results reveal that the observed reduction of time to onset of spreading on gratings A-10 is linked to a massive, early increase of integrin engagement and FAK activation, which in turn mediates the downstream signaling for initial focal complex formation.

Figure Captions of FIGS. 1 Through 9

FIG. 1. Endothelial spreading on COC substrates. A) Differential interference contrast (DIC; upper row) pictures and corresponding cell profiles (white areas on gray background; lower row) extracted from a time-lapse of HUVEC spreading on a flat substrate (total time 60 minutes; _t=1 minute). Cells seeded at t=˜0 rapidly contact the substrate. Onset of spreading takes place at the time when membrane protrusions become visible at the cell-substrate interface (t=30). Black arrowheads pinpoint the position of membrane protrusions. During spreading (t=40), cells increases the surface area in contact with the substrate via sustained membrane ruffling, rapidly reaching a plateau (t=50 and t=60). Corresponding times (in minutes) are reported in the upper left corner of each panel. Scale bar at t=0 corresponds to 20 $\mu m$. B) Dynamics of HUVEC spreading on different substrates. The graph reports the spreading dynamics (normalized to the initial value) of representative individual cells on flat substrates (black line) or on gratings A-1 (dash-dotted black line), A-10 (gray line), B-1 (dashed gray line) and B-10 (dashed black line), respectively.

FIG. 2. Time to onset of spreading and cell alignment to different gratings. A) The histogram reports the time to onset of spreading normalized by the value measured for flat substrates. Note that onset of spreading on gratings A-10 is 40% faster than on flat substrates. The number of analyzed events is reported in the upper right corner. Significant differences between the population means are reported ( indicate $p<0.01$). Error bars represent the measured to standard error of the mean. B) The graph reports the average cell size measured at 1, 2 and 3 hours after seeding for HUVECs contacting flat substrates (black squares) or gratings A-10 (gray circles), A-1 (gray rhombs), B-10 (black stars) and B-1 (black triangles), respectively. The number of analyzed events is reported in the upper right corner. Significant differences between the population means are reported ( indicate $p<0.01$). Error bars represent the measured standard error of the mean. C) The histogram reports the average angle in degrees between cell orientation and the direction of the grating. The graph shows a significant difference for all structured substrates compared with the flat surface substrate. The number of analyzed events is reported in the upper right corner. Significant differences between the population means are reported (** indicate $p<0.01$). Error bars represent the measured standard error of the mean. D) Distribution of filamentous actin in HUVEC spreading on gratings and on flat substrates. The pictures report the inverted fluorescent signal at the cell-substrate-interface as revealed by phalloidin-TRITC staining. Cells on A-10 and B-10 substrates align better than on other tested substrates. In contrast, cells on the flat surface present a typical circular shape. Scale bars correspond to 20 μm. The black arrows indicate the direction of the grating. The corresponding feature sizes of the gratings are defined in Table 1.

FIG. 3. Dynamics of endothelial spreading and circularity on gratings. A) Time-lapse of individual HUVECs spreading on a flat substrate (upper row) or on gratings A-10 (lower row). The pictures report the inverted fluorescent signal at the cell-substrate-interface as revealed by live membrane staining. Corresponding times (in minutes) are reported below the A-10 row. The black arrows indicate the direction of the gratings. B) The graph reports the average spreading dynamics (normalized to the initial value) measured for HUVECs on flat substrates (black squares) or on gratings A-10 (gray circles). Error bars represent the measured standard error of the mean. The number of analyzed events is reported in the lower right corner. C) Cell shape dynamics upon spreading. The graph reports the average circularity of HUVECs upon spreading on flat substrates (black squares) or on gratings A-10 (gray circles). Error bars represent the measured standard error of the mean. The number of analyzed events is reported in the lower right corner.

FIG. 4. Influence of the groove depth on time to onset of spreading and alignment of endothelial cells. A) The histogram reports the time to onset of spreading normalized by the value measured for the flat substrate. Significant differences between the population means are reported ( indicate $p<0.01$). Error bars represent the measured standard error of the mean. The to number of analyzed events is reported in the upper right corner. B) The histogram reports the angle in degrees between cell orientation and the direction of the grating. Significant differences between the population means are reported ( indicate $p<0.01$). Error bars represent the measured standard error of the mean. The number of analyzed events is reported in the upper right corner. C) Scanning electron microscopy images of HUVEC spreading on gratings A-2; D) A-4; E) A-6; F) A-8; and G) A-10. Scale bars correspond to 5 μM. H) Zoom in on membrane protrusions on grating A-6; I) A-8; and L) A-10. Scale bars correspond to 2 μm.

FIG. 5. Focal adhesion maturation on spreading-enhancing topography. A-C) Distribution of vinculin-FRFP fluorescent signal in HUVEC on flat substrates (A) on gratings A-8 (B) and on gratings A-10 (C). The panel shows the inverted fluorescent signal at the cell-substrate-interface. A black rectangle in each panel defines a region of interest encompassing a group of focal adhesions. A zoomed view of the corresponding region of interest is reported as inset in the lower left corner of each panel. Scale bars correspond to 20 μm. The black arrows in panels B and C indicate the direction of the gratings. D-E) Vinculin-FRFP signal intensity (in arbitrary units; a.u.) along the region containing the focal adhesions (lower panels) established on gratings A-8 (D) and A-10 (E). Note that on gratings A-10 the signal peaks are confined to the ridge regions and distributed in periods of 2 μm. F) Distribution of vinculin-FRFP fluorescent signal in HUVECs on gratings A-10 and on flat substrates. The panel shows the inverted fluorescent signal at the cell-substrate-interface. The cell is spreading at the interface between a flat (upper part of the panel) and textured (A-10; lower part of the panel) substrate. Scale bar corresponds to 10 μm. The black arrow in the right panel indicates the direction of the gratings. G) The histogram reports the average size (in μm 2) for focal adhesion established by cells contacting FLAT, A-8 or A-10 substrates, respectively. Significant differences between the population means are reported (** indicate $p<0.01$). Error bars represent the measured standard error of the mean. The number of analyzed events is reported in the upper right corner.

FIG. 6. ROCK1/2 and myosin-II activities are required for contact guidance but dispensable for initial endothelial spreading. A) The histogram reports the time to onset of spreading normalized to the value measured for the flat substrates. Cells were treated with Blebbistatin (Blebb), Y-27632, or ML-7. No spreading could be measured for cells treated with ML-7. All other conditions show a significant difference compared to the flat surface. Significant differences between the population means are reported ( indicate $p<0.01$). Error bars represent to the measured standard error of the mean. The number of analyze events is reported in the upper right corner. B) The histogram reports the angle in degrees between cell orientation and direction of the grating. Significant differences between the population means are reported ( indicate $p<0.01$, * indicates $p<0.05$). Error bars represent the measured standard error of the mean. The number of analyzed events is reported in the upper right corner. C) Distribution of is filamentous actin in HUVEC cells spreading on gratings. All shown scale bars correspond to 20 μm. A black rectangle in each panel defines a region of interest. A zoomed view of the corresponding region of interest is reported as inset in the lower right corner of each panel. The black arrow indicates the direction of the grating.

FIG. 7. Biochemical analysis of integrin signaling on spreading-enhancing topography. A) Analysis of FAK and Src phosphorylation of cells on grating A-10, on flat substrate and of cells kept in suspension. The panels show the Western blots of total and phosphorylated FAK and Src protein levels of cells directly harvested 20 minutes after seeding. B) Western blot quantification of independent experiments. Signals of phosphorylated proteins were always normalized to respective total protein levels. The bars indicate the differences between cells on grating A-10 and cells in suspension with respect to cells on flat substrate (FLAT). Significant differences between the population means are reported (** indicate $p<0.01$). Error bars represent the measured standard error of the mean. C) Localization of pFAK in cells spreading on flat substrate (FLAT) or grating A-10. The pictures report the inverted fluorescent signal at the cell substrate interface as revealed by pFAK staining. A black rectangle in each panel defines a region of interest. A zoomed view of the corresponding region of interest is reported as inset in the lower right corner of each panel. The black arrow in the right panel indicates the direction of the grating. Scale bar corresponds to 20 μm.

Figure 8:
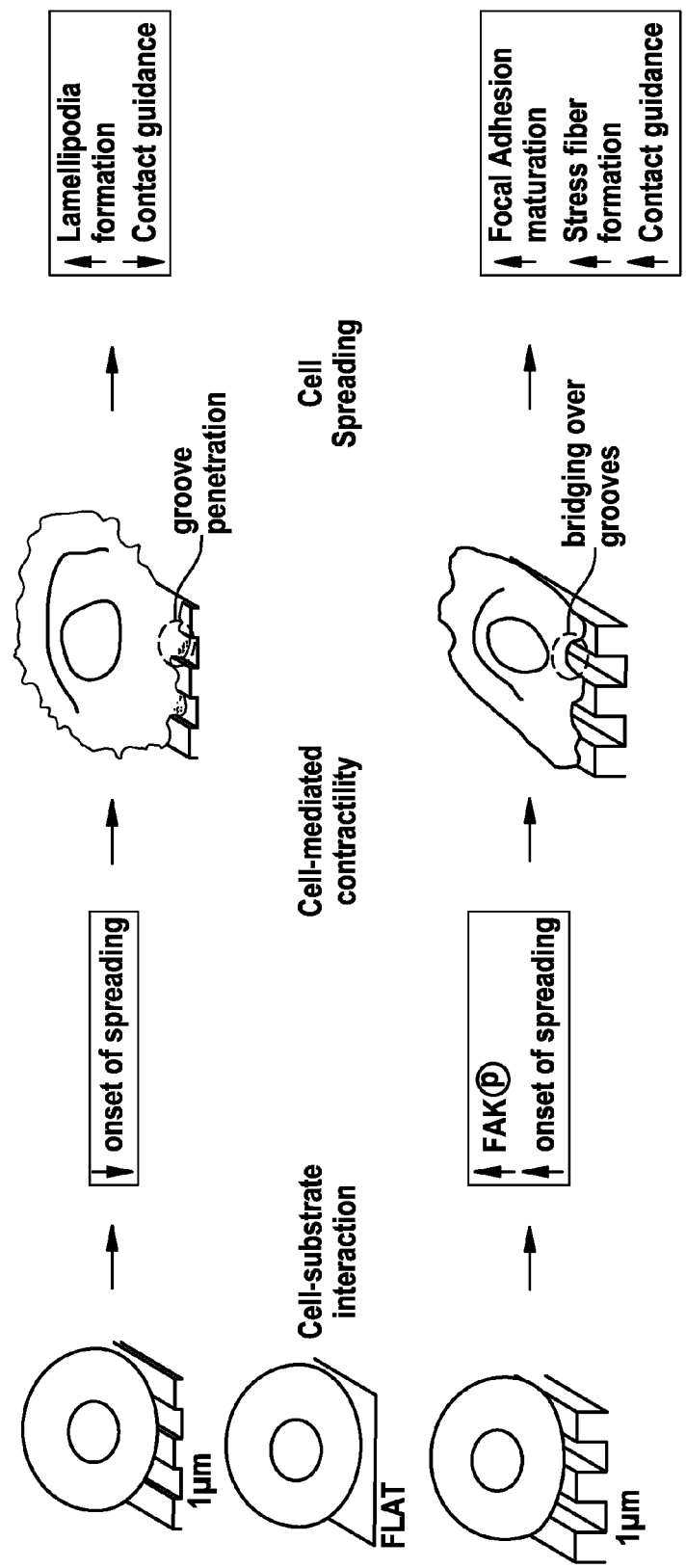
FIG. 8 Model of topographic control of endothelial spreading. Cell-to-substrate interactions modulate the activation of FAK and control the time to onset of spreading.

FIG. 8. Model of topographic control of endothelial spreading. Cell-to-substrate interactions modulate the activation of FAK and control the time to onset of spreading. Once initial adhesions are formed, ROCK and myosin-II mediated cell contractility regulates cells spreading, focal adhesion maturation and remodeling of the actin cytoskeleton. The accessibility of grooves influences these processes, promoting or demoting the onset of spreading dynamics and contact guidance efficiency on shallow (e.g. A-1) or deep (i.e. A-10) gratings when compared to chemically identical flat substrates (FLAT). The time sequence of reported events is depicted by a horizontal gray arrow. The arrows displayed in the squares indicate whether the respective molecular regulators or related cellular activities are promoted or demoted by contact with the respective substrates.

FIG. 9. Fabrication process of COC-gratings. A) Molds were obtained starting from a commercial p-doped silicon wafer. Two examples are shown with ridge and groove width of 1 μm and ridge height of 1 μm (A-10), and with ridge and groove width of 5 μm and ridge height of is 1 μm (B-10), respectively. B) COC foils were placed on top of the silicon mold and softened by increasing the temperature up to 160° C. 50 bar pressure was applied for 10 min before cooling down to 40° C. The pressure was finally released and mold and COC detached. C) High-magnification SEM image of an A-10 grating.

Discussion

Reactions occurring at the interface between cells and anisotropic topographies either promote or demote the onset of spreading of human endothelial cells (FIGS. 1-4). By revealing the cellular machineries which are active at different stages during cell-topography-interaction, we identify two independent phases of this process: First, the onset of spreading is mediated by early integrin signaling through Focal Adhesion Kinase (FIG. 7), and does not require cell generated forces (FIG. 6). Second, the later-stage interaction during contact guidance depends on ROCK1/2 and myosin-II mediated cell contractility (FIG. 6), and on focal adhesion maturation (FIGS. 5 and 7).

Onset of Spreading

The mechanism governing mammalian cell spreading on two-dimensional substrates was largely analysed by experimental and theoretical studies. These works revealed that the spreading of mouse fibroblasts on fibronectin-coated glass proceeds through differently regulated phases including early integrin binding and onset of spreading, fast cells spreading, and focal adhesion formation and substrate traction. While the spreading and adhesion dynamics might, to a certain extent, be cell-type and substrate specific, our results for human endothelial cells contacting COC substrates clearly confirm the existence of an early, focal adhesion and contractility independent stage which can be decoupled from later processes by the use of myosin-II inhibitors (FIG. 6). Onset of spreading in fibroblasts was reported to take place within 30 minutes after seeding and to directly correlate with the density of the fibronectin coating. Human endothelial cells spreading on textured substrates display a similar modulation of the time to onset of spreading as a pure function of the presented surface geometry (FIGS. 1-3). Consistently, we show that once a cell initiates spreading, the spreading velocity is not affected by the substrate identity (FIG. 3). Thus, our results support the hypothesis that besides the ligand concentration, the surface topography acts as an independent parameter contributing to early substrate recognition.

In particular, our data show that the cellular activities leading to onset of spreading are influenced both by the lateral and vertical feature size of the substrate topography (FIGS. 2 and 4). A significant reduction of time to onset of spreading is only observed on gratings with lateral period of 2 μm, 50% duty cycle, and groove depth of 1 μm or deeper. On this particular texture, the interaction between cells and substrate is limited to the ridges (FIGS. 4 and 5). The resulting geometrical constraint produces a periodic engagement of integrins which cluster exclusively on top of the ridges (FIG. 5), while membrane arcs bridge over the grooves. This configuration is rapidly and efficiently converted by the cells into a biochemical signal via the activation of Focal Adhesion Kinase (FIG. 7) and leads to adhesion maturation (FIG. 5) and cell polarization along the gratings (FIGS. 3 and 4). In this frame, integrin clustering in laterally confined regions may trigger the downstream adhesion cascade more efficiently. Indeed, integrin clustering on periodically-spaced adhesive patterns controls adhesion formation and spreading in fibroblasts. On the other hand, the kinase activity of Src does not change significantly upon cell interaction with the substrate (FIG. 7). This result may be explained by the presence of an overriding alternative signal. In this vision, the sustained signaling by growth factors in the medium may contribute to maintain high levels of Src activation before and after the onset of spreading.

Contact Guidance

The elongation of cells and their polarization along the direction of gratings (alternating lines of ridges and grooves) was reported for several cellular models, including fibroblasts, neurons, epithelial and endothelial cells. The features size range at which contact guidance is most efficient varies from cell to cell.

In our experimental setup the observation that onset of spreading and contact guidance are differently sensitive to the vertical size of the tested gratings (FIG. 4) indicates that different cellular activities are involved. In particular, the effect on onset of spreading (FIG. 1) is not to affected by the inhibition of myosin-II mediated cell contractility (FIG. 6). Thus, the mechanical linkage between adhesions and the actin cytoskeleton is not required at this stage (FIG. 3). On the other hand, cell-mediated contractility is required for focal adhesion maturation. Importantly, efficient contact guidance requires focal adhesions maturation indicating a link between the two processes (FIG. 6). We recently demonstrated that alignment to anisotropic topographies results from the topographical constraint of focal adhesion maturation and is driven by ROCK1/2 and myosin-II mediated cell contractility. Indeed, when this pathway is selectively blocked, the measured effect on contact guidance is lost (FIG. 6).

Altogether our results support a model in which a topographical modification of the substrate with a specific geometry influences the interaction between endothelial cells and the surface at two different stages: onset of spreading and contact guidance (FIG. 8). Immediately after establishment of physical contact between the cell and the substrate, the topography limits cell contact on top of ridges and triggers a biochemical signal via Focal Adhesion Kinase, which contributes to adhesion establishment and maturation. This activity eventually re-shapes the cell cytoskeleton along the gratings, inducing efficient polarization.

CONCLUSIONS

We have identified a topographic modification of biocompatible substrates that enhances their endothelialization. Our results demonstrate that the coverage of target surfaces by human endothelial cells is strongly modulated by the lateral and vertical feature size of anisotropic topographies. Early reactions occurring at the interface between cells and grooved surfaces either promote or demote the spreading of endothelial cells. Importantly, by indentifying the cellular machineries which are active at different stages during cell-to-topography interaction, we have discovered two independent phases of this process. While the effect on onset of spreading is mediated by early integrin signaling through Focal Adhesion Kinase, the later interaction during contact guidance depends on ROCK1/2 and myosin-II mediated cell contractility, and on focal adhesion maturation.

In summary, the resulting model paves the way to an improved design of cardiovascular implants yielding a faster and more efficient re-endothelialization.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implant formed as a stent, comprising a main body having a plurality of struts covered with a surface layer configured for accelerated onset of cell spreading with directional cell growth against the flow of blood, wherein the surface layer has a topographic modification of a line pattern with ridge and groove widths of 0.9 to 1.1 μm and a ridge height of 0.8 to 2.0 μm, wherein the line pattern is aligned orthogonal to a stent strut direction.

2. The implant of claim 1, wherein the main body is made of a metallic material and the surface layer is made of a polymer material.

3. The implant of claim 2, wherein the metallic material is a biodegradable metallic material.

4. The implant of claim 3, wherein the biodegradable metallic material is selected from the group consisting of a magnesium alloy, iron alloy, magnesium and iron.

5. The implant of claim 2, wherein the polymer material is a biodegradable polymer material.

6. The implant of claim 1, wherein the line pattern of the surface layer is covered by a biodegradable topcoat.

7. The implant of claim 1, wherein an angle between a groove bottom surface and a side wall of the ridge is between 90° to 135°.

8. The implant of claim 7, wherein the ridge and groove widths are 1 μm and the ridge height is 1 μm.

9. The implant of claim 1, wherein the line pattern covers at least a luminal surface of the stent.

10. The implant of claim 1, wherein the stent is a drug eluting stent.

11. The implant of claim 1, wherein the line pattern is a pattern of uninterrupted grooves and ridges or is a pattern of grooves and ridges deteriorated to less than 40% from the uninterrupted grooves and ridges.

12. The implant of claim 1, wherein the line pattern is oriented orthogonal to implant geometry.

13. The implant of claim 1, wherein the ridge and groove widths are 1 μm and the ridge height is 1 μm.

* * * * *